US009051453B2

(12) United States Patent
Sugahara et al.

(10) Patent No.: US 9,051,453 B2
(45) Date of Patent: Jun. 9, 2015

(54) POLYPEPTIDE SOLUTION, ARTIFICIAL POLYPEPTIDE FIBER PRODUCTION METHOD AND POLYPEPTIDE PURIFICATION METHOD USING SAME

(71) Applicant: SPIBER INC., Tsuruoka-shi, Yamagata (JP)

(72) Inventors: Junichi Sugahara, Tsuruoka (JP); Kazuhide Sekiyama, Tsuruoka (JP); Ryota Sato, Tsuruoka (JP); Kaori Sekiyama, Tsuruoka (JP); Mizuki Ishikawa, Tsuruoka (JP); Shinya Murata, Tsuruoka (JP); Kazuko Otomo, Tsuruoka (JP)

(73) Assignee: SPIBER INC., Yamagata (JP)

( * ) Notice: Subject to any disclaimer, the term of this patent is extended or adjusted under 35 U.S.C. 154(b) by 0 days.

(21) Appl. No.: 14/346,893

(22) PCT Filed: Oct. 29, 2012

(86) PCT No.: PCT/JP2012/077920
§ 371 (c)(1),
(2) Date: Mar. 24, 2014

(87) PCT Pub. No.: WO2013/065650
PCT Pub. Date: May 10, 2013

(65) Prior Publication Data
US 2014/0245923 A1     Sep. 4, 2014

(30) Foreign Application Priority Data

Nov. 2, 2011     (JP) .................................. 2011-241486

(51) Int. Cl.
*C07K 14/435*     (2006.01)
*B29D 99/00*      (2010.01)
*C08K 5/41*       (2006.01)
*C08K 5/20*       (2006.01)
*D01D 5/04*       (2006.01)
*D01F 4/02*       (2006.01)
*C08K 3/16*       (2006.01)

(52) U.S. Cl.
CPC ... *C08K 5/41* (2013.01); *C08K 5/20* (2013.01); *D01D 5/04* (2013.01); *D01F 4/02* (2013.01); *C07K 14/43518* (2013.01); *B29D 99/0078* (2013.01); *C08K 3/16* (2013.01); *Y10S 530/858* (2013.01)

(58) Field of Classification Search
CPC ...... C07K 14/43518; C08K 3/16; C08K 5/20; C08K 5/41; B29D 99/0078
USPC ........... 106/124.4; 264/177.19, 202; 530/344, 530/418, 858
See application file for complete search history.

(56) References Cited

U.S. PATENT DOCUMENTS

| 6,620,917 | B1 | 9/2003 | Mello et al. |
| 7,014,802 | B1* | 3/2006 | Eby et al. ..................... 264/46.5 |
| 7,335,739 | B2 | 2/2008 | Mello et al. |
| 8,568,637 | B2* | 10/2013 | Gazit et al. .................... 264/202 |
| 2003/0201560 | A1* | 10/2003 | Vollrath et al. ................. 264/41 |
| 2005/0158821 | A1 | 7/2005 | Mello et al. |
| 2007/0092558 | A1* | 4/2007 | Heavner et al. .............. 424/450 |
| 2011/0046686 | A1* | 2/2011 | Kaplan et al. ............... 606/86 R |
| 2011/0136669 | A1 | 6/2011 | Liebmann et al. |

FOREIGN PATENT DOCUMENTS

| CN | 101564914 | 10/2009 |
| CN | 101721739 | 6/2010 |
| CN | 102181948 | 9/2011 |
| JP | 11-217506 | 8/1999 |
| JP | 2972877 B | 11/1999 |
| JP | 2004-503204 | 2/2004 |
| JP | 2006-257000 | 9/2006 |
| WO | WO 01/53333 | 7/2001 |
| WO | WO 2007/078239 | 7/2007 |
| WO | WO 2010/015419 | 2/2010 |

OTHER PUBLICATIONS

Kearns et al, "Silk-based Biomaterials for Tissue Engineering", Topics in Tissue Engineering, vol. 4, 2008, pp. 1-19.*
Sekiyama: "Artificial Synthesis of Dream Fiber "Spider Silk""; the Journal of the Japanese Society for Cutaneous Health, Aug. 2011, No. 66, pp. 1-10 with its partial English translation (13 pages).
Sugihara et al.: "Artificial Production of Spider Silk Fibers"; Polymer Preprints, Japan, 2011, vol. 60, No. 22, pp. 5338-5339 with its partial English translation (6 pages).
Teule et al.: "A protocol for the production of recombinant spider silk-like proteins for artificial fiber spinning"; Nature Protocols, 2009, vol. 4, No. 3, pp. 341-355.
Heim et al.: "Spider Silk: From Soluble Protein to Extraordinary Fiber", Angewandte. Chem. Int. Ed., 2009, vol. 48, No. 20, pp. 3584-3596.

(Continued)

*Primary Examiner* — David M Brunsman
(74) *Attorney, Agent, or Firm* — Hamre, Schumann, Mueller & Larson, P.C.

(57) ABSTRACT

A polypeptide solution of the present invention is a polypeptide solution in which a polypeptide derived from natural spider silk proteins is dissolved in a solvent. The solvent contains at least one selected from the following (i)-(iii): (i) DMSO; (ii) DMSO with an inorganic salt; and (iii) DMF with an inorganic salt. Further, in the present invention, an artificial polypeptide fiber is obtained by: using the polypeptide solution as a dope solution; and extruding the dope solution from a spinneret into a desolvation bath so as to eliminate the solvent from the dope solution and form a fiber to produce an undrawn yarn. Moreover, in the present invention, a polypeptide is purified by subjecting the polypeptide solution to heat treatment and thereafter removing an undissolved substance therefrom. Thus, the present invention provides the polypeptide solution whose solute has high solubility and solvent itself is low cost, and that allows dissolution at high temperatures and has high safety: a method for producing an artificial polypeptide fiber: and a method for purifying a polypeptide.

17 Claims, 9 Drawing Sheets

(56) References Cited

OTHER PUBLICATIONS

Diao, et al., "Solubility and Electrospun Regenerated Fiber of Two Different Kinds of Spider Silk", Journal of Materials Science & Engineering, vol. 26, No. 6, Dec. 2008, pp. 918-922 with an English abstract.

Sashina, et al., "Structure and solubility of natural silk fibroin", Russian Journal of Applied Chemistry, vol. 79, No. 6, Jun. 1, 2006, pp. 869-876.

Grip, et al., "Engineered disulfides improve mechanical properties of recombinant spider silk" Protein Science, vol. 18, Jan. 1, 2009, pp. 1012-1022.

In Chul Um, et al., "Wet spinning of silk polymer I. Effect of coagulation conditions on the morphological feature of filament", International Journal of Biological Macromolecules, vol. 34, No. 1-2, Apr. 1, 2004, pp. 89-105.

Hardy, et al., "Polymeric materials based on silk proteins", Polymer, vol. 49, No. 20, Sep. 23, 2008, pp. 4309-4327.

Fu, et al., "Animal silks: their structures, properties and artificial production", Chemical Communications, vol. 43, Jan. 1, 2009, pp. 6515-6529.

Hardy, et al., "Composite materials based on silk proteins", Progress in Polymer Science, vol. 35, No. 9, Sep. 1, 2010, pp. 1093-1115.

Vepari, et al., "Silk as a biomaterial", Progress in Polymer Science, vol. 32, No. 8-9, Aug. 7, 2007, pp. 991-1007.

Lazaris, et al., "Spider Silk Fibers Spun from Soluble Recombinant Silk Produced in Mammalian Cells", Science, vol. 295, No. 5554, Jan. 18, 2002, pp. 472-476.

\* cited by examiner

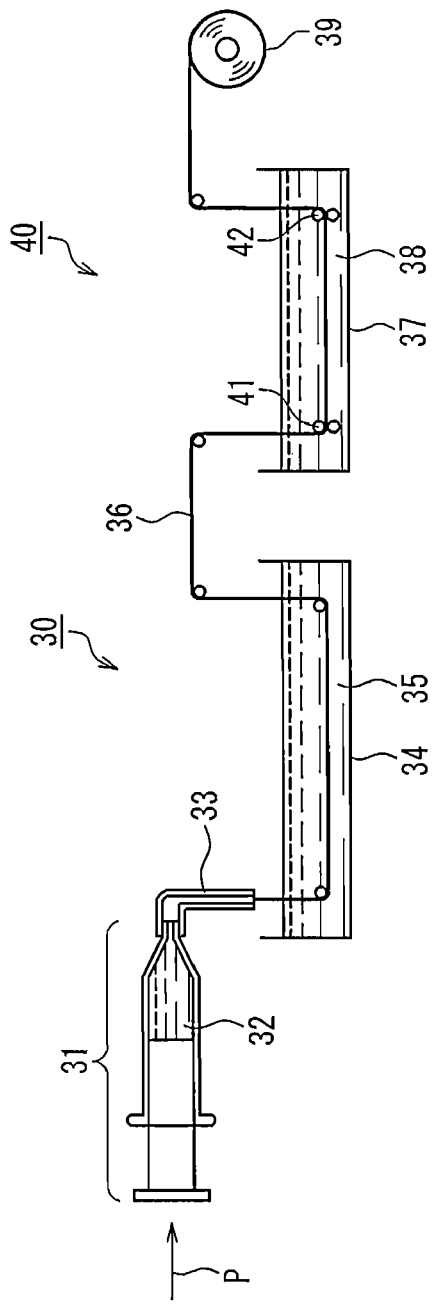
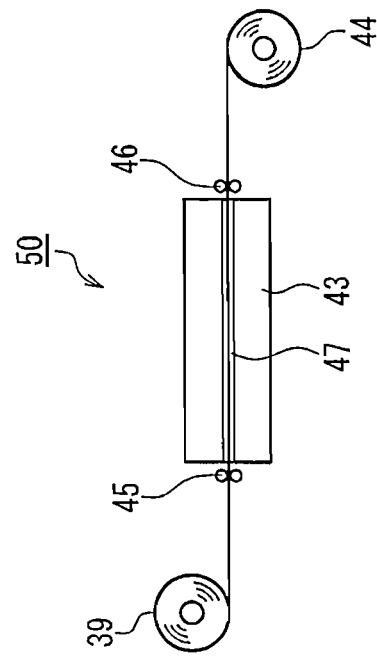
FIG. 2A
FIG. 2B

POLYPEPTIDE SOLUTION, ARTIFICIAL POLYPEPTIDE FIBER PRODUCTION METHOD AND POLYPEPTIDE PURIFICATION METHOD USING SAME

This application is a 371 of PCT/JP2012/077920, filed Oct. 29, 2012.

TECHNICAL FIELD

The present invention relates to a polypeptide solution in which a polypeptide is dissolved in a particular solvent, and a method for producing an artificial polypeptide fiber and a method for purifying a polypeptide using the same.

BACKGROUND ART

Spider silk fibers are fibers having strength and stretchability, and are known to have higher toughness than high-tensile steels, Nylon 6 (trademark) fibers, and the like. In addition, they have an advantage in that oil is not used as a raw material and biomass can be used instead. Some artificial spider silk fibers also have been proposed. For example, Patent Document 1 describes a fiber obtained by using, as a spinning solution, a solution in which a synthetic protein derived from natural spider silk proteins is dissolved in hexafluoroisopropanol (HFIP), and subjecting the solution to wet spinning.

PRIOR ART DOCUMENT

Patent Document

Patent Document 1: JP 2004-503204 A

DISCLOSURE OF INVENTION

Problem to be Solved by the Invention

However, conventional solvents such as hexafluoroisopropanol (HFIP) that are used for artificial polypeptides derived from natural spider silk proteins are expensive, and have problems of safety.

In order to solve the above-described conventional problems, the present invention provides a polypeptide solution whose solute has high solubility and solvent itself is low cost, and that has a higher boiling point than water to allow dissolution at high temperatures and has high safety: and a method for producing an artificial polypeptide fiber and a method for purifying a polypeptide using the same.

Means for Solving Problem

A polypeptide solution of the present invention is a polypeptide solution in which a polypeptide derived from natural spider silk proteins is dissolved in a solvent, wherein the solvent contains at least one selected from the following (i)-(iii):
 (i) Dimethyl sulfoxide;
 (ii) Dimethyl sulfoxide with an inorganic salt; and
 (iii) N,N-dimethylformamide with an inorganic salt.

A method for producing an artificial polypeptide fiber of the present invention is a method for producing an artificial polypeptide fiber using the above-described polypeptide solution, including: using the polypeptide solution as a dope solution; and extruding the dope solution from a spinneret into a coagulation liquid in a desolvation bath so as to eliminate a solvent from the dope solution and form a fiber to prepare an undrawn yarn, thereby obtaining an artificial polypeptide fiber.

A method for purifying a polypeptide of the present invention is a method for purifying a polypeptide using the above-described polypeptide solution, including: subjecting the polypeptide solution to heat treatment and thereafter removing an undissolved substance therefrom.

Effect of the Invention

The polypeptide solution of the present invention is a solution in which a polypeptide (hereinafter, also referred to as a solute) derived from natural spider silk proteins is dissolved in a solvent. By addition of at least one substance selected from (i)-(iii) above to the solvent, the solute can have high solubility, the polypeptide solution can have a high boiling point, which allows dissolution at high temperatures, and have high safety, and the cost of the solvent itself can be reduced. If the solute has high solubility and is soluble at high concentration, the productivity of fibers and films can be increased by using the polypeptide solution as a dope solution. If dissolution at high temperatures is possible, the dope solution can be adjusted efficiently. Further, if the boiling point is higher than that of water, it can be used also as a polymerization solvent for causing a dehydration condensation reaction. If the safety is high, the production workability can be increased, and further the application can be broader. Moreover, the polypeptide solution has spinnability, and hence is useful for wet spinning, cast film, etc. Moreover, polypeptides can be purified easily using the polypeptide solution.

BRIEF DESCRIPTION OF DRAWINGS

FIGS. 2A and 2B illustrate production devices in another example of the present invention. FIG. 2A shows a spinning device and a first-stage drawing device, and FIG. 2B shows a second-stage drawing device.

FIG. 4A shows a spinning device, and FIG. 4B shows a drawing device.

DESCRIPTION OF THE INVENTION

Figure 1:
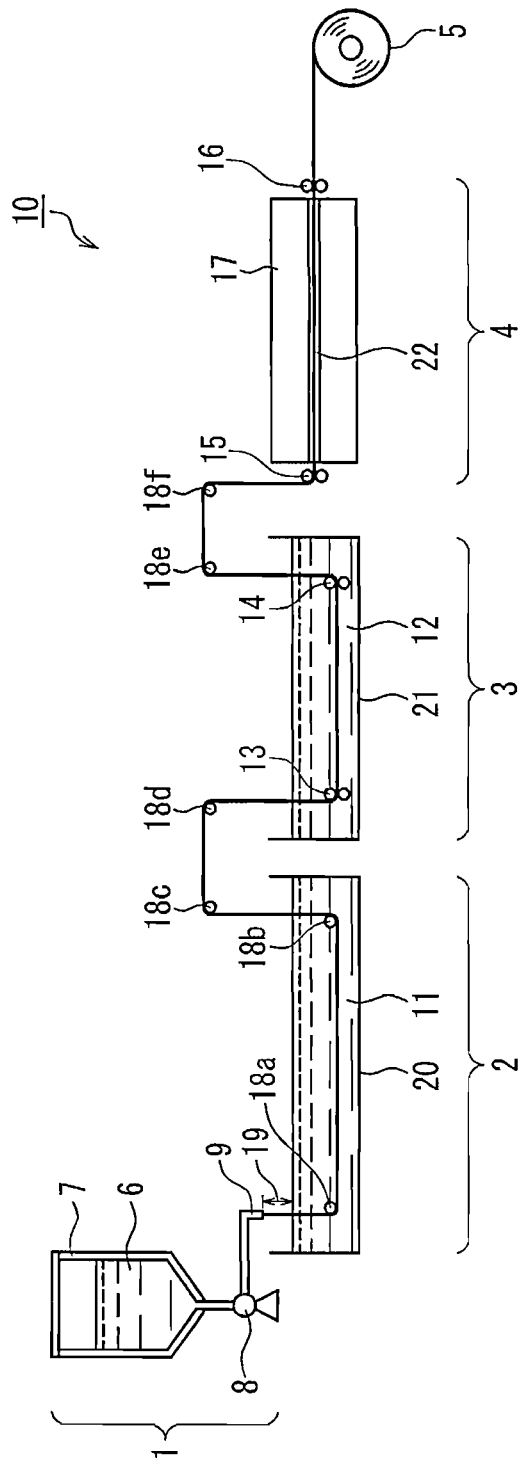
FIG. 1 illustrates a production device in one example of the present invention.

1. Solvent (1) Selection of Polar Solvent

The inventors of the present invention examined what kind of solvents would be suitable for dissolving polypeptides derived from natural spider silk proteins to obtain a polypeptide solution, and mainly selected polar solvents to perform solubility experiments. As a result, it was found that solvents containing any of the substances described in (i)-(iii) above had high solubility selectively and allowed dissolution at high temperatures. When the polypeptide solution is 100 mass %, the solute concentration (solubility) is preferably 3 mass % (w/v %) or more, more preferably 15 mass % or more, and further preferably 40 mass % or more. Further, the solute concentration is preferably 45 mass % or less. Dimethyl sulfoxide (DMSO) has a melting point of 18.4° C. and a boiling point of 189° C. N,N-dimethylformamide (DMF) has a melting point of −61° C. and a boiling point of 153° C. DMSO and DMF have much higher boiling points than hexafluoroisopropanol (HFIP) and hexafluoroacetone (HFAc) having boiling points of 59° C. and −26.5° C., respectively, which have been used in conventional methods. Further, in view of the fact that DMSO and DMF have been used also in general industrial fields for acrylic fiber polymerization and acrylic fiber spinning solutions, etc., and as solvents for polyimide polymerization, they are low cost substances with proven safety.

(2) Dissolution Promoter

Adding an inorganic salt to DMSO or DMF is preferable because it further increases the solubility of the solute. The inorganic salt is preferably at least one selected from alkali metal halides (e.g., LiCl, LiBr, etc), alkaline-earth metal halides (e.g., $CaCl_2$, etc.), alkaline-earth metal nitrate (e.g., $Ca(NO_3)_2$, etc.), and thiocyanate (e.g., NaSCN, etc.). When the solvent is 100 mass %, the percentage of the inorganic salt preferably ranges from 0.1 to 20 mass %.

(3) Purity of Solvent, Additive

The solvent may contain alcohol and/or water in addition to the substances described in (i)-(iii) above.

When the solvent is 100 mass %, the percentage of the substances described in (i)-(iii) above is 22 mass % or more and 100 mass % or less. The remainder may contain alcohol. In the above description, "alcohol" preferably is a lower alcohol with a carbon number of 1 to 6, and more preferably at least one kind selected from the group consisting of methanol, ethanol, and 2-propanol. In the case of containing water, the percentage of the substances described in (i)-(iii) above is 10 mass % or more and 100 mass % or less when the solvent is 100 mass %. The remainder may be water. Water and alcohol may be mixed together.

2. Polypeptide

In the present invention, as a polypeptide, a polypeptide derived from natural spider silk proteins is used, for example. The polypeptide is not limited particularly as long as it is derived from natural spider silk proteins, and examples of the polypeptide include natural spider silk proteins and recombinant spider silk proteins such as variants, analogs, derivatives or the like of the natural spider silk proteins. In terms of excellent tenacity, the polypeptide preferably is derived from major dragline silk proteins produced in major ampullate glands of spiders. Examples of the major dragline silk proteins include major ampullate spidroin MaSp1 and MaSp2 from Nephila clavipes, and ADF3 and ADF4 from Araneus diadematus, etc. Examples of the polypeptide derived from major dragline silk proteins include variants, analogs, derivatives or the like of the major dragline silk proteins. Further, the polypeptide may be derived from flagelliform silk proteins produced in flagelliform glands of spiders. Examples of the flagelliform silk proteins include flagelliform silk proteins derived from Nephila clavipes, etc.

Examples of the polypeptide derived from major dragline silk proteins include a polypeptide containing two or more units of an amino acid sequence represented by the formula 1: REP1-REP2 (1), preferably a polypeptide containing five or more units thereof, and more preferably a polypeptide containing ten or more units thereof. Alternatively, the polypeptide derived from major dragline silk proteins may be a polypeptide that contains units of the amino acid sequence represented by the formula 1: REP1-REP2 (1) and that has, at a C-terminal, an amino acid sequence represented by any of SEQ ID NOS: 1 to 3 or an amino acid sequence having a homology of 90% or more with the amino acid sequence represented by any of SEQ ID NOS: 1 to 3. In the polypeptide derived from major dragline silk proteins, units of the amino acid sequence represented by the formula 1: REP1-REP2 (1) may be the same or may be different from each other. In the case of producing a recombinant protein using a microbe such as *Escherichia coli* as a host, the molecular weight of the polypeptide derived from major dragline silk proteins is preferably 500 kDa or less, more preferably 300 kDa or less, and further preferably 200 kDa or less, in terms of productivity.

In the formula (1), the REP1 indicates polyalanine. In the REP1, the number of alanine residues arranged in succession is preferably 2 or more, more preferably 3 or more, further preferably 4 or more, and particularly preferably 5 or more. Further, in the REP1, the number of alanine residues arranged in succession is preferably 20 or less, more preferably 16 or less, further preferably 12 or less, and particularly preferably 10 or less. In the formula (1), the REP2 is an amino acid sequence composed of 10 to 200 amino acid residues. The total number of glycine, serine, glutamine and alanine residues contained in the amino acid sequence is 40% or more, preferably 60% or more, and more preferably 70% or more with respect to the total number of amino acid residues contained therein.

In the major dragline silk, the REP1 corresponds to a crystal region in a fiber where a crystal β sheet is formed, and the REP2 corresponds to an amorphous region in a fiber where most of the parts lack regular configurations and that has more flexibility. Further, the [REP1-REP2] corresponds to a repetitious region (repetitive sequence) composed of the crystal region and the amorphous region, which is a characteristic sequence of dragline silk proteins.

An amino acid sequence represented by SEQ ID NO: 1 is identical to an amino acid sequence that is composed of 50 amino acid residues of an amino acid sequence of ADF3 at the C-terminal (NCBI Accession No.: AAC47010, GI: 1263287). An amino acid sequence represented by SEQ ID NO: 2 is identical to an amino acid sequence represented by SEQ ID NO: 1 from which 20 residues have been removed from the C-terminal. An amino acid sequence represented by SEQ ID NO: 3 is identical to an amino acid sequence represented by SEQ ID NO: 1 from which 29 residues have been removed from the C-terminal.

An example of the polypeptide that contains units of the amino acid sequence represented by the formula 1: REP1-REP2 (1) and that has, at a C-terminal, an amino acid sequence represented by any of SEQ ID NOS: 1 to 3 or an amino acid sequence having a homology of 90% or more with the amino acid sequence represented by any of SEQ ID NOS: 1 to 3 is a polypeptide having an amino acid sequence represented by SEQ ID NO: 8. The polypeptide having the amino acid sequence represented by SEQ ID NO: 8 is obtained by the following mutation: in an amino acid sequence of ADF3 (NCBI Accession No.: AAC47010, GI: 1263287) to the N-terminal of which has been added an amino acid sequence (SEQ ID NO: 5) composed of a start codon, His 10 tags and an HRV3C Protease (Human rhinovirus 3C Protease) recognition site, $1^{st}$ to $13^{th}$ repetitive regions are about doubled and the translation ends at the $1154^{th}$ amino acid residue. In the polypeptide having the amino acid sequence represented by SEQ ID NO: 8, the C-terminal sequence is identical to the amino acid sequence represented by SEQ ID NO: 3.

Further, the polypeptide that contains units of the amino acid sequence represented by the formula 1: REP1-REP2 (1) and that has, at a C-terminal, an amino acid sequence represented by any of SEQ ID NOS: 1 to 3 or an amino acid sequence having a homology of 90% or more with the amino acid sequence represented by any of SEQ ID NOS: 1 to 3 may be a protein that has an amino acid sequence represented by SEQ ID NO: 8 in which one or a plurality of amino acids have been substituted, deleted, inserted and/or added and that has a repetitious region composed of a crystal region and an amorphous region. In the present invention, "one or a plurality of" refers to 1 to 40, 1 to 35, 1 to 30, 1 to 25, 1 to 20, 1 to 15, 1 to 10, or 1 or a few, for example. Further, in the present invention, "one or a few" refers to 1 to 9, 1 to 8, 1 to 7, 1 to 6, 1 to 5, 1 to 4, 1 to 3, 1 to 2, or 1.

Further, an example of the polypeptide containing two or more units of the amino acid sequence represented by the formula 1: REP1-REP2 (1) is a recombinant protein derived from ADF4 having an amino acid sequence represented by SEQ ID NO: 15. The amino acid sequence represented by SEQ ID NO: 15 is an amino acid sequence obtained by adding the amino acid sequence (SEQ ID NO: 5) composed of a start codon, His 10 tags and an HRV3C Protease (Human rhinovirus 3C Protease) recognition site, to the N-terminal of a partial amino acid sequence of ADF4 obtained from the NCBI database (NCBI Accession No.: AAC47011, GI: 1263289). Further, the polypeptide containing two or more units of the amino acid sequence represented by the formula 1: REP1-REP2 (1) may be a polypeptide that has an amino acid sequence represented by SEQ ID NO: 15 in which one or a plurality of amino acids have been substituted, deleted, inserted and/or added and that has a repetitious region composed of a crystal region and an amorphous region. Further, an example of the polypeptide containing two or more units of the amino acid sequence represented by the formula 1: REP1-REP2 (1) is a recombinant protein derived from MaSp2 that has an amino acid sequence represented by SEQ ID NO: 17. The amino acid sequence represented by SEQ ID NO: 17 is an amino acid sequence obtained by adding the amino acid sequence (SEQ ID NO: 5) composed of a start codon, His 10 tags and an HRV3C Protease (Human rhinovirus 3C Protease) recognition site, to the N-terminal of a partial sequence of MaSp2 obtained from the NCBI web database (NCBI Accession No.: AAT75313, GI: 50363147). Furthermore, the polypeptide containing two or more units of the amino acid sequence represented by the formula 1: REP1-REP2 (1) may be a polypeptide that has an amino acid sequence represented by SEQ ID NO: 17 in which one or a plurality of amino acids have been substituted, deleted, inserted and/or added and that has a repetitious region composed of a crystal region and an amorphous region.

Examples of the polypeptide derived from flagelliform silk proteins include a polypeptide containing 10 or more units of an amino acid sequence represented by the formula 2: REP3 (2), preferably a polypeptide containing 20 or more units thereof, and more preferably a polypeptide containing 30 or more units thereof. In the case of producing a recombinant protein using a microbe such as *Escherichia coli* as a host, the molecular weight of the polypeptide derived from flagelliform silk proteins is preferably 500 kDa or less, more preferably 300 kDa or less, and further preferably 200 kDa or less, in terms of productivity.

In the formula (2), the REP 3 indicates an amino acid sequence composed of Gly-Pro-Gly-Gly-X, where X indicates an amino acid selected from the group consisting of Ala, Ser, Tyr and Val.

A major characteristic of the spider silk is that the flagelliform silk does not have a crystal region, but has a repetitious region composed of an amorphous region. Since the major dragline silk and the like have a repetitious region composed of a crystal region and an amorphous region, they are expected to have both high stress and stretchability. Meanwhile, as to the flagelliform silk, although the stress is inferior to that of the major dragline silk, the stretchability is high. The reason for this is considered to be that most of the flagelliform silk is composed of amorphous regions.

An example of the polypeptide containing 10 or more units of the amino acid sequence represented by the formula 2: REP3 (2) is a recombinant protein derived from flagelliform silk proteins having an amino acid sequence represented by SEQ ID NO: 19. The amino acid sequence represented by SEQ ID NO: 19 is an amino acid sequence obtained by combining a partial sequence of flagelliform silk protein of Nephila clavipes obtained from the NCBI database (NCBI Accession No.: AAF36090, GI: 7106224), specifically, an amino acid sequence thereof from the $1220^{th}$ residue to the $1659^{th}$ residue from the N-terminal that corresponds to repetitive sections and motifs (referred to as a PR1 sequence), with a partial sequence of flagelliform silk protein of Nephila clavipes obtained from the NCBI database (NCBI Accession No.: AAC38847, GI: 2833649), specifically, a C-terminal amino acid sequence thereof from the $816^{th}$ residue to the $907^{th}$ residue from the C-terminal, and thereafter adding the amino acid sequence (SEQ ID NO: 5) composed of a start codon, His 10 tags and an HRV3C Protease recognition site, to the N-terminal of the combined sequence. Further, the polypeptide containing 10 or more units of the amino acid sequence represented by the formula 2: REP3 (2) may be a polypeptide that has an amino acid sequence represented by SEQ ID NO: 19 in which one or a plurality of amino acids have been substituted, deleted, inserted and/or added and that has a repetitious region composed of an amorphous region.

The polypeptide can be produced using a host that has been transformed by an expression vector containing a gene encoding a polypeptide. A method for producing a gene is not limited particularly, and it may be produced by amplifying a gene encoding a natural spider silk protein from a cell derived from spiders by a polymerase chain reaction (PCR), etc., and cloning it, or may be synthesized chemically. Also, a method for chemically synthesizing a gene is not limited particularly, and it can be synthesized as follows, for example: based on information of amino acid sequences of natural spider silk proteins obtained from the NCBI web database, etc., oligonucleotides that have been synthesized automatically with AKTA oligopilot plus 10/100 (GE Healthcare Japan Corporation) are linked by PCR, etc. At this time, in order to facilitate the purification and observation of protein, it is possible to synthesize a gene that encodes a protein having an amino acid sequence of the above-described amino acid sequence to the N-terminal of which has been added an amino acid sequence composed of a start codon and His 10 tags.

Examples of the expression vector include a plasmid, a phage, a virus, and the like that can express protein based on a DNA sequence. The plasmid-type expression vector is not limited particularly as long as it allows a target gene to be expressed in a host cell and it can amplify itself. For example, in the case of using *Escherichia coli* Rosetta (DE3) as a host, a pET22b(+) plasmid vector, a pCold plasmid vector, and the like can be used. Among these, in terms of productivity of protein, it is preferable to use the pET22b(+) plasmid vector. Examples of the host include animal cells, plant cells, microbes, etc.

The polypeptide used in the present invention is preferably a polypeptide derived from ADF3, which is one of two principal dragline silk proteins of Araneus diadematus. This polypeptide has advantages of basically having high strength-elongation and toughness and of being synthesized easily.

3. Polypeptide Solution (1) Preparation of Polypeptide Solution

The polypeptide solution is prepared by adding a solvent to the above-described polypeptide. The solvent contains any of the substances described in (i)-(iii) above. Alternatively, the solvent contains, in addition to any of the substances described in (i)-(iii) above, water and/or alcohol. The polypeptide solution can be used as a dope solution. The dope solution is useful for wet spinning, a cast film solution, etc. The dope solution is produced by adjusting the viscosity of the polypeptide solution for spinning. For example, the viscosity of the polypeptide solution is adjusted to 100 to 10,000 cP (centipoises) so as to obtain the dope solution. The viscosity of the polypeptide solution can be adjusted, for example, by adjusting the concentration of the polypeptide in the solution. The viscosity of the polypeptide solution is measured, for example, using "EMS Viscometer" (product name) manufactured by Kyoto Electronics Manufacturing Co., Ltd. Note that the polypeptide solution of the present invention may contain inevitable components, such as impurities contained in the polypeptide.

(2) Polymerization of Polypeptide Using Polypeptide Solution

The boiling point of the dope solution of the present invention is higher than that of water, and hence is suitable for causing a dehydration condensation reaction therein. For example, before use of the solution for wet spinning, cast film, and the like, polymerizing polypeptides dissolved in the polypeptide solution through dehydration condensation enlarges the polypeptides, thereby enhancing the strength and toughness of fibers and films to be obtained. Adding the solvent that contains any of the substances described in (i)-(iii) above to the above-described polypeptide and heating the solution at 100° C. or higher causes the dehydration condensation between polypeptides, resulting in polymerization of the polypeptides. At this time, by inducing the reaction under the conditions of reflux, reduced pressure, vacuum conditions, etc., the polymerization efficiency can be enhanced. Further, the polymerization efficiency can be enhanced dramatically by using a known dehydration condensation catalyst in combination. When polymerizing polypeptides through the dehydration condensation reaction using the polypeptide solution, desirably a polypeptide main chain is extended by dehydration condensation between a $NH_2$ group of a polypeptide molecular terminal and a COOH group of another polypeptide molecular terminal. Therefore, side chains of a polypeptide to be used preferably contain as few functional groups ($NH_2$ group, COOH group, OH group, SH group) as possible, and most preferably contain no functional group. The number of these functional groups can be adjusted by adjusting the percentage of amino acids to be used. The polypeptide solution that has been subjected to the above-described polymerization reaction can be used directly, or can be diluted appropriately by adding the substances described in (i)-(iii) above, ethyl alcohol, methyl alcohol, water, or the like, for wet spinning, cast film production, etc.

4. Wet Spinning-Drawing (1) Wet Spinning

Wet spinning is adopted for spinning. By this method, the solvent dissolving a polymer is removed from a dope solution (also called as desolvation or coagulation), whereby fibers are formed and an undrawn yarn is obtained. A coagulation liquid to be used for wet spinning is not limited particularly as long as it allows desolvation. Preferably, the coagulation liquid for eliminating a solvent and forming fibers is a lower alcohol with a carbon number of 1 to 5, such as methanol, ethanol and 2-propanol, or acetone. Water may be added appropriately. The temperature of the coagulation liquid preferably is 5-30° C. This range stabilizes spinning. By extruding the above-described spinning solution from a spinneret into the coagulation liquid in a desolvation bath, an undrawn yarn is obtained. In the case of using a syringe pump with a nozzle 0.1-0.6 mm in diameter, the extrusion speed preferably is 0.2-6.0 ml/h per one hole. A more preferable extrusion speed is 1.4-4.0 ml/h per one hole. This range stabilizes spinning. It is preferable that the length of the desolvation bath (coagulation liquid bath) is 200-500 mm, the take-up speed of the undrawn yarn is 1-14 m/min, and the residence time is 0.01-0.15 min. A more preferable take-up speed of the undrawn yarn is 1-3 m/min. These ranges allow efficient desolvation. Drawing (pre-drawing) may be performed in the coagulation liquid. However, taking into consideration the evaporation of a lower alcohol, it is preferable to maintain the coagulation liquid at low temperature so as to take up yarns in an undrawn state.

(2) Drawing

Drawing may be performed either in one stage or in two or more stages (multistage drawing). Since the molecules of the polypeptides derived from natural spider silk proteins are less likely to be oriented, the multistage drawing is performed so as to orient the molecules stepwise and increase the total draw ratio. Consequently, fibers with high toughness can be obtained.

FIGS. 1 and 2 are examples of the multistage drawing. FIG. 1 shows a continuous process of spinning and drawing. A spinning-drawing device 10 includes an extruder 1, an undrawn-yarn production device 2, a wet-heat drawing device 3, and a dry-heat drawing device 4. A spinning solution 6 is stored in a storage tank 7 and extruded from a spinneret 9 by a gear pump 8. In a laboratory scale, a spinning solution may be filled in a cylinder and extruded from a nozzle using a syringe pump. The extruded spinning solution is supplied directly or via an air gap 19 into a coagulation liquid 11 in a coagulation liquid bath 20, so as to remove a solvent. Thereafter, an obtained undrawn yarn is supplied into hot water 12 in a drawing bath 21 and subjected to the first-stage drawing. The draw ratio depends on the speed ratio between a supply nip roller 13 and a take-up nip roller 14. Next, the yarn is supplied to a dry-heat drawing device 17 and subjected to the second-stage drawing inside a guide 22, whereby a yarn roll 5 is prepared. The draw ratio depends on the speed ratio between a supply nip roller 15 and a take-up nip roller 16. 18*a* to 18*f* are yarn guides.

FIGS. 2A and 2B are an example of the two-stage drawing. FIG. 2A shows a spinning device 30 and a first-stage drawing device 40, and FIG. 2B shows a second-stage drawing device 50. In each device, a yarn may be wound, or may be stored in a container without being wound. In the spinning device 30, a spinning solution 32 is contained in a microsyringe 31 and moved in a direction indicated by an arrow P using a syringe pump, whereby the spinning solution 32 is extruded from a nozzle 33 and supplied into a coagulation liquid 35 in a coagulation liquid bath 34. Thus, an undrawn yarn 36 is prepared. Subsequently, in the first-stage drawing device 40, the undrawn yarn 36 is supplied into hot water 38 in a drawing bath 37 and subjected to the first-stage drawing, whereby a yarn roll 39 of the first-stage drawn yarn is prepared. The draw ratio depends on the speed ratio between a supply nip roller 41 and a take-up nip roller 42. Next, the first-stage drawn yarn is unwound from the yarn roll 39, supplied to a dry-heat drawing device 43, and subjected to the second-stage drawing inside a guide 47. The draw ratio depends on the speed ratio between a supply nip roller 45 and a take-up nip roller 46. Then, the drawn yarn is wound as a yarn roll 44.

Figure 3:
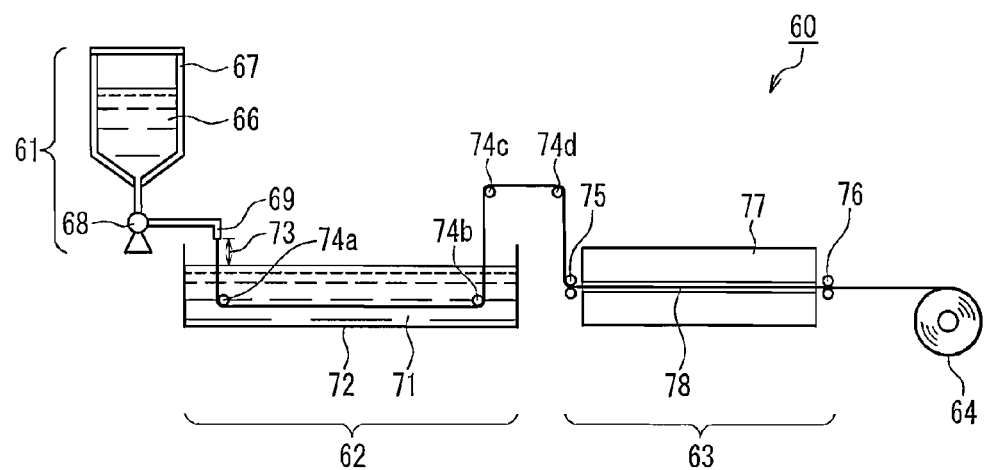
FIG. 3 illustrates a production device in still another example of the present invention.

FIGS. 3 and 4 are examples of the one-stage drawing. FIG. 3 shows a continuous process of spinning and drawing. A spinning-drawing device 60 includes an extruder 61, an undrawn-yarn production device 62, and a dry-heat drawing device 63. A spinning solution 66 is stored in a storage tank 67 and extruded from a spinneret 69 by a gear pump 68. In a laboratory scale, a spinning solution may be filled in a cylinder and extruded from a nozzle using a syringe pump. The extruded spinning solution is supplied directly or via an air gap 73 into a coagulation liquid 71 in a coagulation liquid bath 72, so as to remove a solvent. Then, an obtained undrawn yarn is supplied into a dry-heat drawing device 77 and drawn inside a guide 78, whereby a yarn roll 64 is prepared. The draw ratio depends on the speed ratio between a supply nip roller 75 and a take-up nip roller 76. 74a to 74f are yarn guides.

Figure 4A:
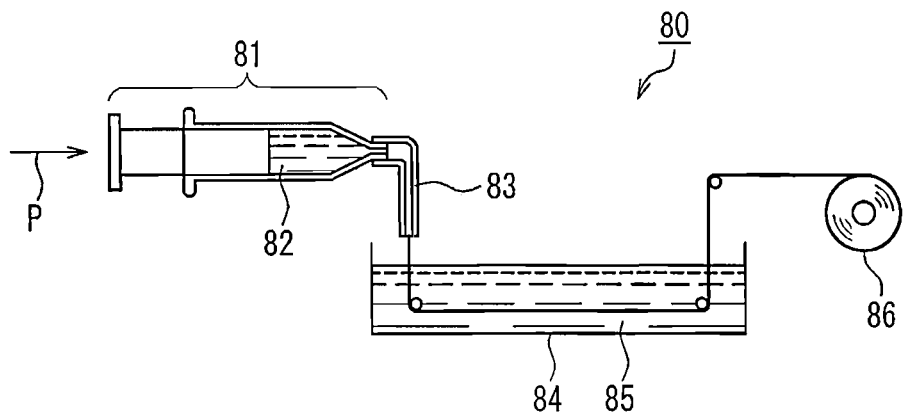
FIGS. 4A and 4B illustrate production devices in still another example of the present invention.
Figure 4B:
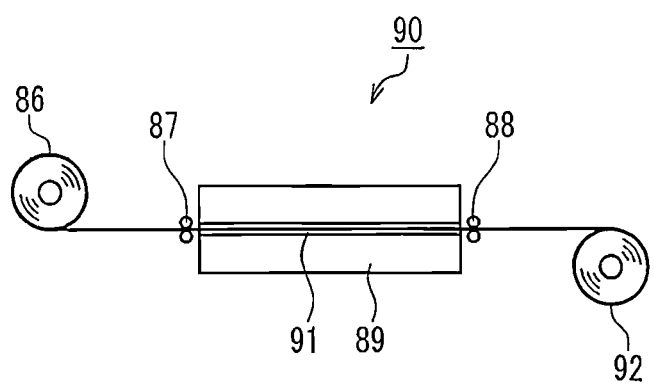

FIGS. 4A and 4B illustrate a case where spinning and drawing are separated. FIG. 4A shows a spinning device 80, and FIG. 4B shows a drawing device 90. In each device, a yarn may be wound, or may be stored in a container without being wound. In the spinning device 80, a spinning solution 82 is contained in a microsyringe 81, moved in a direction indicated by an arrow P using a syringe pump, extruded from a nozzle 83, and supplied into a coagulation liquid 85 in a coagulation liquid bath 84. Thus, a yarn roll 86 of the undrawn yarn is prepared. Subsequently, in the drawing device 90, the undrawn yarn is unwound from the yarn roll 86, supplied to a dry-heat drawing device 89, and drawn inside a guide 91. The draw ratio depends on the speed ratio between a supply nip roller 87 and a take-up nip roller 88. Next, the drawn yarn is wound as a yarn roll 92. Thus, a drawn yarn is obtained.

The diameter of the artificial polypeptide fiber obtained in the wet spinning-drawing preferably ranges from 5 to 100 µm. This range allows stable fiber production. The fiber diameter more preferably ranges from 8 to 50 µm, and further preferably ranges from 10 to 30 µm. The cross section of the artificial polypeptide fiber obtained in the wet spinning-drawing is not limited to a round shape and may have various shapes. Therefore, the fiber diameter as used herein refers to an average diameter under the assumption that the cross section is round.

5. Cast Film

The polypeptide solution of the present invention can be formed into a cast film as a dope solution. For example, the dope solution may be cast in a predetermined thickness on a plate that is resistant to the solvent in the dope solution such as a glass plate, and the solvent is eliminated from the cast film, whereby an artificial polypeptide film is obtained. In order to cast the dope solution in a predetermined thickness, the solution is cast in a thickness of several microns or more using a jig such as a doctor coater and a knife coater, and thereafter the solvent is eliminated by being dried under reduced pressure or by being immersed in a desolvation bath. Thus, a cast film is obtained.

6. Cross-Linking

For the artificial polypeptide fiber or the film of the present invention, cross-links may be formed chemically between polypeptide molecules. Examples of functional groups that can be used for the polypeptide cross-linking include amino groups, carboxyl groups, thiol groups, and hydroxy groups, though they are not limited to these. An amino group of a lysine side chain contained in a polypeptide can be cross-linked with a carboxyl group of a glutamic acid or an aspartic acid side chain via amide bonds by dehydration condensation. Cross-links may be formed by a dehydration condensation reaction under vacuum heating, or by a dehydration condensation agent such as carbodiimide. Also, a cross-linking agent such as glutaraldehyde may be used. Further, an enzyme such as transglutaminase may be used to form cross-links. As one example, a cross-linking reaction may be caused using a cross-linking agent such as carbodiimide, glutaraldehyde, and polyfunctional epoxy resin (as one example, "Denacol" (product name) manufactured by Nagase ChemteX Corporation). Carbodiimide is represented by the general formula: $R^1N=C=NR^2$ (where $R^1$ and $R^2$ indicate an organic group containing an alkyl group with a carbon number of 1 to 6, or a cycloalkyl group), and specific compounds thereof include 1-ethyl-3-(3-dimethylaminopropyl)carbodiimide hydrochloride (EDC), N,N'-dicyclohexylcarbodiimide (DCC), 1-cyclohexyl-3-(2-morpholinoethyl)carbodiimide, diisopropyl carbodiimide (DIC), etc. Among these, EDC and DIC are preferred because they have a high ability to form amide bonds of peptide chains and hence cause cross-linking reactions easily. Regarding the cross-linking treatment, cross-links may be formed by adding a cross-linking agent to a dope solution, or by applying a cross-linking agent to drawn yarns and subjecting the yarns to vacuum heating-drying. The cross-linking agent may be applied to fibers in a pure form (100 mass %), or may be diluted using a lower alcohol with a carbon number of 1 to 5, buffer solution or the like, and thereafter applied to fibers at a concentration of 0.005 to 10 mass %. Regarding the conditions for the treatment, preferably the temperature is 20 to 45° C. and the time is 3 to 42 hours. The cross-linking treatment using the cross-linking agent increases the strength, toughness, chemical resistance, etc., of artificial polypeptide drawn fibers.

7. Polypeptide Purification Method

Polypeptides can be purified using the above-described polypeptide solution. Especially when polypeptides are insoluble proteins, a high effect can be obtained. In the present invention, "insoluble proteins" refer to water-insoluble proteins, i.e., proteins with high hydrophobicity. Specifically, the polypeptide solution is prepared by adding the solvent containing any of the substances (i)-(iii) above to the polypeptide derived from natural spider silk proteins, dissolving the polypeptide by heat treatment and collecting a supernatant. The conditions for the heat treatment are not limited particularly as long as insoluble proteins can be dissolved but are not decomposed. For example, the temperature of the heat treatment is preferably 45° C. or higher, and more preferably 50° C. or higher, in terms of solubility. Further, in terms of suppressing the decomposition, the temperature of the heat treatment is preferably 100° C. or lower, and more preferably 95° C. or lower. The heat treatment time is preferably 15 to 300 minutes, and more preferably 30 to 180 minutes, for example. Moreover, the collection of a supernatant is not limited particularly as long as a precipitate can be separated. For easy handling, the separation preferably is performed through filtration or centrifugation. The separation through filtration can be performed using a filter paper, a filtration membrane, etc., for example. The conditions for centrifugation are not limited particularly, and it may be performed at 11000×g for 5 minute, for example.

When the polypeptide derived from natural spider silk proteins is a recombinant spider silk protein, it is preferable to wash the recombinant spider silk protein with an anionic surfactant such as SDS before addition of a solvent, in terms of enhancing the purification degree. Specifically, a host cell expressing the recombinant spider silk protein is disrupted so as to extract as a precipitate an insoluble protein fraction that contains the recombinant spider silk protein, and the extracted insoluble protein containing the recombinant spider silk protein is washed with an anionic surfactant.

As described above, since the polypeptide solution in which the polypeptide derived from natural spider silk proteins is dissolved in the above-described solvent can be used as a dope solution, the polypeptide solution purified according to the above-described polypeptide purification method need not be powdered by freeze-drying, and can be used for a dope solution directly.

EXAMPLES

Hereinafter, the present invention will be described in further detail by way of examples. Note that the present invention is not limited to the following examples.

(Recombinant Spider Silk Protein)
<Gene Synthesis>
(1) Gene Synthesis of ADF3Kai A partial amino acid sequence of ADF3, which is one of two principal dragline silk proteins of Araneus diadematus, was obtained from the NCBI web database (NCBI Accession No.: AAC47010, GI: 1263287), and synthesis of a gene encoding an amino acid sequence (SEQ ID NO: 6) was outsourced to GenScript, Inc. The amino acid sequence (SEQ ID NO: 6) is an amino acid sequence obtained by adding the amino acid sequence (SEQ ID NO: 5) composed of a start codon, His 10 tags and an HRV3C Protease (Human rhinovirus 3C Protease) recognition site, to the N-terminal of said partial amino acid sequence of ADF3. Consequently, a pUC57 vector to which a gene of ADF3Kai having a base sequence represented by SEQ ID NO: 7 had been introduced was obtained (having an Nde I site immediately upstream of 5' terminal of the gene and an Xba I site immediately downstream of 5' terminal thereof). Thereafter, said gene was subjected to a restriction enzyme treatment with Nde I and EcoR I, and recombined into a pET22b(+) expression vector.

(2) Gene Synthesis of ADF3Kai-Large

The half of the gene sequence of ADF3Kai on the 5' side (hereinafter, referred to as a sequence A) was amplified by the PCR reaction using ADF3Kai as a template, and a T7 promoter primer (SEQ ID NO: 11) and a Rep Xba I primer (SEQ ID NO: 12). The obtained DNA fragment of the sequence A was recombined into a pUC118 vector that in advance had been subjected to the restriction enzyme treatment with Nde I and Xba I using a Mighty Cloning Kit (manufactured by TAKARA BIO INC.). Similarly, the half of the gene sequence of ADF3Kai on the 3' side (hereinafter, referred to as a sequence B) was amplified by the PCR reaction using ADF3Kai as a template, and an Xba I Rep primer (SEQ ID NO: 14) and a T7 terminator primer (SEQ ID NO: 13). The obtained DNA fragment of the sequence B was recombined into a pUC118 vector that in advance had been subjected to the restriction enzyme treatment with Xba I and EcoR I using the Mighty Cloning Kit (manufactured by TAKARA BIO INC.). The pUC118 vector to which the sequence A had been introduced and the pUC118 vector to which the sequence B had been introduced were subjected to the restriction enzyme treatment with Nde I, Xba I and Xba I, EcoR I, respectively, and target DNA fragments of the sequences A and B were purified by gel cut. The DNA fragments A, B and the pET22b(+) that in advance had been subjected to the restriction enzyme treatment with Nde I and EcoR I were subjected to a ligation reaction and transformed into Escherichia coli DH5α. After confirming the insertion of the target DNA fragments by a colony PCR using a T7 promoter primer and a T7 terminator primer, plasmid was extracted from a colony where a target band size (3.6 kbp) was obtained, and the entire base sequence was checked by a sequence reaction using a 3130×1 Genetic Analyzer (Applied Biosystems). Consequently, the construction of a gene of ADF3Kai-Large represented by SEQ ID NO: 9 was confirmed. The amino acid sequence of ADF3Kai-Large is as represented by SEQ ID NO: 4.

(3) Gene Synthesis of ADF3Kai-Large-NRSH1

With a pET22b(+) vector to which the gene of ADF3Kai-Large obtained above had been introduced used as a template, through Site-Directed Mutagenesis using a PrimeSTAR Mutagenesis Basal Kit (manufactured by TAKARA BIO INC.), a codon GGC corresponding to the $1155^{th}$ amino acid residue, i.e., glycine (Gly), in the amino acid sequence of ADF3Kai-Large (SEQ ID NO: 4) was mutated into a stop codon TAA, and a gene of ADF3Kai-Large-NRSH1 represented by SEQ ID NO: 10 was constructed on the pET22b(+). The accuracy of the introduction of the mutation was checked by the sequence reaction using the 3130×1 Genetic Analyzer (Applied Biosystems). The amino acid sequence of ADF3Kai-Large-NRSH1 is as represented by SEQ ID NO: 8.

(4) Gene Synthesis of ADF4Kai

A partial amino acid sequence of ADF4, which is one of two principal dragline silk proteins of Araneus diadematus, was obtained from the NCBI web database (NCBI Accession No.: AAC47011, GI: 1263289), and a gene encoding a protein ADF4Kai having an amino acid sequence (SEQ ID NO: 15) was synthesized. The amino acid sequence (SEQ ID NO: 15) is an amino acid sequence obtained by adding the amino acid sequence (SEQ ID NO: 5) composed of a start codon, His 10 tags and an HRV3C Protease recognition site, to the N-terminal of said partial amino acid sequence of ADF4. Consequently, a pUC57 vector to which a gene of ADF4Kai having a base sequence represented by SEQ ID NO: 16 had been introduced was obtained (having an Nde I site immediately upstream of 5' terminal of the gene and an Xba I site immediately downstream of 5' terminal thereof). Thereafter, said gene was subjected to the restriction enzyme treatment with Nde I and EcoR I, and recombined into a pET22b(+) expression vector. Thus, a pET22b(+) vector to which the gene of ADF4Kai had been introduced was obtained.

(5) Gene Synthesis of MaSp2_N

A partial amino acid sequence of major ampullate spidroin (MaSp2) of Nephila clavipes was obtained from the NCBI web database (NCBI Accession No.: AAT75313, GI: 50363147), and a gene encoding a protein MaSp2_N having an amino acid sequence (SEQ ID NO: 17) was synthesized. The amino acid sequence (SEQ ID NO: 17) is an amino acid sequence obtained by adding the amino acid sequence (SEQ ID NO: 5) composed of a start codon, His 10 tags and an HRV3C Protease recognition site, to the N-terminal of said partial amino acid sequence of MaSp2_N. Consequently, a pUC57 vector to which a gene of MaSp2_N having a base sequence represented by SEQ ID NO: 18 had been introduced was obtained (having an Nde I site immediately upstream of 5' terminal of the gene and an Xba I site immediately downstream of 5' terminal thereof). Thereafter, said gene was subjected to the restriction enzyme treatment with Nde I and EcoR I, and recombined into a pET22b(+) expression vector. Thus, a pET22b(+) vector to which the gene of MaSp2_N had been introduced was obtained.

(6) Gene Synthesis of Flag__92_short2

A partial sequence of flagelliform silk protein of Nephila clavipes was obtained from the NCBI web database (NCBI Accession No.: AAF36090, GI: 7106224), and the amino acid sequence from the $1220^{th}$ residue to the $1659^{th}$ residue from the N-terminal, which corresponds to repetitive sections and motifs, was selected (referred to as a PR1 sequence). Further, a partial sequence of flagelliform silk protein of Nephila clavipes was obtained from the NCBI web database (NCBI Accession No.: AAC38847, GI: 2833649), and the C-terminal amino acid sequence from the $816^{th}$ residue to the $907^{th}$ residue from the C-terminal was selected (referred to as a C-terminal NR). A gene encoding a protein Flag__92_short2 having an amino acid sequence (SEQ ID NO: 19) was synthesized. The amino acid sequence (SEQ ID NO: 19) is an amino acid sequence obtained by adding the amino acid sequence (SEQ ID NO: 5) composed of a start codon, His 10 tags and an HRV3C Protease recognition site, to the N-terminal of the combined sequence of the PR1 sequence and the C-terminal NR. Consequently, a pUC57 vector to which a gene of Flag__92_short2 having a base sequence represented by SEQ ID NO: 20 had been introduced was obtained (having an Nde I site immediately upstream of 5' terminal of the gene and an Xba I site immediately downstream of 5' terminal thereof). Thereafter, said gene was subjected to the restriction enzyme treatment with Nde I and EcoR I, and recombined into a pET22b(+) expression vector. Thus, a pET22b(+) vector to which the gene of Flag__92_short2 had been introduced was obtained.

<Expression of Protein>

The pET22b(+) expression vector containing the gene sequence of ADF3Kai-Large-NRSH1, the pET22b(+) expression vector containing the gene sequence of ADF4Kai, the pET22b(+) expression vector containing the gene sequence of MaSp2_N, and the pET22b(+) expression vector containing the gene sequence of Flag__92_short2 were each transformed into *Escherichia coli* Rosetta (DE3). The obtained single colony was incubated for 15 hours in 2 mL of an LB culture medium containing ampicillin. Thereafter, 1.4 ml of said culture solution was added to 140 mL of an LB culture medium containing ampicillin, and incubated to an $OD_{600}$ of 3.5 under the conditions of 37° C. and 200 rpm. Next, the culture solution with the $OD_{600}$ of 3.5 was added to 7 L of a 2×YT culture medium containing ampicillin together with 140 mL of 50% glucose, and incubated further to the $OD_{600}$ of 4.0. Thereafter, isopropyl-β-thiogalactopyranoside (IPTG) was added to the obtained culture solution with the $OD_{600}$ of 4.0 so that the final concentration became 0.5 mM, thereby inducing the expression of protein. After a lapse of two hours from the addition of IPTG, the culture solution was centrifuged and bacterial cells were collected. Protein solutions prepared from the culture solutions before the addition of IPTG and after the addition of IPTG were each electrophoresed in a polyacrylamide gel. Consequently, target band sizes (ADF3Kai-Large-NRSH1: about 101.1 kDa; ADF4Kai: about 37.7 kDa; MaSp2_N; about 31.7 kDa; and Flag__92_short2: about 46.6 kDa) were observed with the addition of IPTG, and the expression of the target protein was confirmed. *Escherichia coli* expressing the ADF3Kai-Large-NRSH1 protein, *Escherichia coli* expressing the ADF4Kai protein, *Escherichia coli* expressing the MaSp2_N protein, and *Escherichia coli* expressing the Flag__92_short2 protein were stored in a freezer (−20° C.).

Example 1

(1) Used Protein (I) About 4.5 g of bacteria cells of the *Escherichia coli* expressing the ADF3Kai-Large-NRSH1 protein and 30 ml of a buffer solution AI (20 mM Tris-HCl, pH 7.4) were added to a centrifuge tube (50 ml). After dispersing the bacteria cells with a mixer ("SI-0286" manufactured by GE, level 10), the dispersion was centrifuged (10,000 rpm, 10 minutes, room temperature) with a centrifuge ("MX-305" manufactured by TOMY SEIKO Co., Ltd.), and a supernatant was discarded.

(II) To a precipitate (bacteria cells) obtained by the centrifugation, 30 ml of the buffer solution AI and 0.3 ml of 0.1 M PMSF (dissolved by isopropanol) were added. After dispersing the precipitate for 3 minutes with the above-described mixer (level 10) manufactured by GE, the bacteria cells were disrupted using an ultrasonic disrupter ("VCX500" manufactured by Sonics & Materials, Inc.) and centrifuged (10,000 rpm, 10 minutes, room temperature).

(III) To a precipitate obtained by the centrifugation, 30 mL of the buffer solution AI was added. After dispersing the precipitate for 3 minutes with a mixer ("T18 basic ULTRA TURRAX" manufactured by IKA, level 2), the dispersion was centrifuged (10,000 rpm, 10 minutes, room temperature) with the above-described centrifuge manufactured by TOMY SEIKO Co., Ltd., and a supernatant was removed.

(IV) To the centrifuge tube from which the supernatant was discarded, a 7.5 M urea buffer solution I (7.5 M urea, 10 mM sodium dihydrogen phosphate, 20 mM NaCl, 1 mM Tris-HCl, pH 7.0) was added, and a precipitate was dispersed well with the above-described ultrasonic disrupter (level 7) manufactured by SMT. Thereafter, the precipitate was dissolved for 120 minutes with a shaker (200 rpm, 60° C.) manufactured by TAITEC CORPORATION. The protein solution after dissolution was centrifuged (11,000×g, 10 minutes, room temperature) with the above-described centrifuge manufactured by TOMY SEIKO Co., Ltd., and a supernatant was dialyzed with water using a dialysis tube (cellulose tube 36/32 manufactured by Sanko Junyaku Co., Ltd.). Aggregate protein (white) obtained after dialysis was collected by centrifugation, and water was removed by a freeze dryer, so as to collect freeze-dried powder. The purification degree of the target protein ADF3Kai-Large-NRSH1 (about 101.1 kDa) in the obtained freeze-dried powder was checked by analyzing images of the results of polyacrylamide gel electrophoresis (CBB staining) of said protein powder using Totallab (nonlinear dynamics Ltd.). As a result, the purification degree of ADF3Kai-Large-NRSH1 was about 85%.

2. Solvent (1) Polar Solvent

As the solvent, polar solvents that are used for acrylic fiber polymerization and acrylic fiber spinning solutions, and as solvents for polyimide polymerization were examined mainly.

DMA: N,N-dimethylacetamide
DMF: N,N-dimethylformamide
DMI: 1,3-dimethyl-2-imidazolidinone
NMP: N-methyl-2-pyrrolidone
HFIP: hexafluoroisopropanol
DMSO: dimethyl sulfoxide
Formic acid
Butylene carbonate Propylene carbonate
γ-butyrolactone
Hexamethyl phosphoramide
(2) Dissolution Promoter (Inorganic Salt)
The following inorganic salts were examined.
Alkali metal halides: LiCl, LiBr
Alkaline-earth metal halide: $CaCl_2$
Alkaline-earth metal nitrate: $Ca(NO_3)_2$
Sodium thiocyanate: NaSCN
<Experiment 1>
As shown in Table 1, the solubility tests were performed using systems that added inorganic salts to polar solvents. The temperature was set at 100° C. The concentration of the polypeptide (protein) derived from natural spider silk proteins was set at 4 mass %. The solubility evaluations shown in Table 1 and in subsequent Tables below were performed based on the following standards. In Table 1, the mass % of the inorganic salt is the mass ratio of the inorganic salt relative to the total mass of the polar solvent and the inorganic salt.
[Solubility Evaluation Standards]
A: Dissolved
B: Mostly dissolved, but undissolved substances remained partially
C: Undissolved Further, the systems that added any of ethyl alcohol, methyl alcohol and ultrapure water to the substances (i)-(iii) above also were found to have high solubility.

Next, the spinnability was examined with respect to the solvents that had been ranked A in the solubility evaluation standards in Table 1. Wet spinning was adopted for the spinnability tests. Whether or not undrawn yarns could be produced under the following conditions was a criterion for judging the spinnability: in the spinning process shown in FIG. 4A, the spinning solution was filled in a cylinder and extruded from a nozzle 0.3 mm in diameter at a speed of 2.0 ml/h using a syringe pump, and thereafter the solvent was extracted in a 100 mass % methanol coagulation liquid. The length of the coagulation liquid bath was 250 mm, and the take-up speed was 2.1 m/min. Consequently, all the solvents that had been ranked A in the solubility evaluation standards in Table 1 had spinnability.

<Experiment 2>
An experiment of increasing the concentration of the polypeptide (protein) derived from natural spider silk proteins was performed. It was checked whether proteins at concentrations of 40 mass %, 45 mass % and 50 mass % could

TABLE 1

| Polar solvent | Inorganic salt | (mass %) | Solubility | Solubility in the case of using additive (mass %) | | | | | |
|---|---|---|---|---|---|---|---|---|---|
| | | | | EtOH*1 | | MeOH*1 | | Ultrapure water | |
| DMSO | Without salt | | A | 23 | A | 14 | A | 90 | A |
| | LiCl | 10 | A | 60 | A | 52 | A | 90 | A |
| | LiBr | 10 | A | 33 | A | 30 | A | 90 | A |
| | $Ca(NO_3)_2$ | 95.5 | A | 74 | A | 78 | A | 90 | A |
| | $CaCl_2$ | 13.6 | A | 57 | A | 39 | A | 90 | A |
| | NaSCN | 13.6 | A | 33 | A | 25 | A | 90 | A |
| DMF | Without salt (~150° C.) | | C | —*4 | | — | | — | |
| | LiCl | 14.4 | A | 62 | A | 45 | A | 90 | A |
| | LiBr | 10 | A | 27 | A | 21 | A | 90 | A |
| | $Ca(NO_3)_2$ | 77.7 | A | 72 | A | 67 | A | 90 | A |
| | $CaCl_2$ | 7.1 | A | 25 | A | 14 | A | 90 | A |
| | NaSCN | 27.8 | A | 36 | A | 35 | A | 90 | A |
| HFIP*2 | Without salt | | A | 47 | A | 38 | A | 40 | A |
| DMA | Without salt | | C | — | | — | | — | |
| | LiCl | 11.1 | C | — | | — | | — | |
| NMP | Without salt | | C | — | | — | | — | |
| | LiCl | 10 | C | — | | — | | — | |
| DMI | Without salt | | C | — | | — | | — | |
| | LiCl | 14.2 | C | — | | — | | — | |
| Butylene carbonate | Without salt | | C | — | | — | | — | |
| | LiCl | 8.7 | C | — | | — | | — | |
| Propylene carbonate | Without salt | | C | — | | — | | — | |
| | LiCl | 8.3 | C | — | | — | | — | |
| Ethylene carbonate | Without salt | | C | — | | — | | — | |
| | LiCl | 7.7 | C | — | | — | | — | |
| γ-butyrolactone | Without salt | | C | — | | — | | — | |
| | LiCl | 8.9 | C | — | | — | | — | |
| Hexamethyl PhosPhoramide | Without salt | | C | — | | — | | — | |
| | LiCl | 9.7 | C | — | | — | | — | |
| Formic acid*3 | Without salt | | Decomposed | — | | — | | — | |
| | LiCl | 29.1 | Decomposed | — | | — | | — | |

(Note 1) EtOH indicates ethyl alcohol, and MeOH indicates methyl alcohol.
(Note 2) Since HFIP has a low boiling point, the dissolution was performed at 37° C. Further, no salt (LiCl) could be dissolved in HFIP.
(Note 3) The decomposition of protein by formic acid was confirmed by a mass spectrum.
(Note 4) In Table 1, [—] means that no experiment was performed.

As is apparent from Table 1, the solvents containing any of (i)-(iii) below were found to be superior selectively.
(i) Dimethyl sulfoxide: DMSO
(ii) Dimethyl sulfoxide: DMSO with an inorganic salt
(iii) N,N-dimethylformamide: DMF with an inorganic salt be dissolved in solvents at 100° C. Table 2 shows the results. Incidentally, dissolved solutions of DMF (LiCl concentration: 14.4 mass %) and DMSO (LiCl concentration: 10 mass %) were stable even if they are lowered to room temperature (25° C.), and kept the dissolved state.

TABLE 2

| Protein concentration (mass %) | Without addition of LiCl | | | With addition of LiCl | | | LiCl concentration (mass %) |
|---|---|---|---|---|---|---|---|
| | 40 | 45 | 50 | 40 | 45 | 50 | |
| Formic acid | Decomposed*1 | —*3 | — | Decomposed*1 | — | — | 29.1 |
| DMF | — | — | — | A | A | B | 14.4 |
| DMSO | — | — | — | A | B | B | 10 |
| HFIP*2 | B | B | B | — | — | — | 0.2 or less |

(Note 1) The decomposition of protein by formic acid was confirmed by a mass spectrum.
(Note 2) Since HFIP has a low boiling point, the dissolution was performed at 37° C.
(Note 3) In Table 2, [—] means that no experiment was performed.

From Table 2, it was found that addition of the inorganic salt to DMSO allowed the protein to be dissolved sufficiently and favorably up to 40 mass % (the boundary of solubility was 43 mass %), and addition of the salt to DMF allowed the protein to be dissolved sufficiently and favorably up to 45 mass % (the boundary of solubility was 48 mass %).

<Experiment 3>

Next, the protein was dissolved at 100° C. using DMSO, and the temperature was kept at 100° C. or the temperature of the polypeptide solution was decreased to low temperatures and maintained for three hours so as to observe the stability. Table 3 shows the results.

TABLE 3

| LiCl concentration (mass %) | Protein concentration (mass %) | Temperature (° C.) | | | |
|---|---|---|---|---|---|
| | | 25 | 50 | 80 | 100 |
| 0 | 20 | Gel | Gel | A | A |
| | 25 | Gel | Gel | A | A |
| 0.9 | 20 | Gel | B | A | A |
| 2.7 | 20 | Gel | A | A | A |
| 3.6 | 20 | A | A | A | A |
| | 30 | Gel | B | B | A |
| | 45 | Gel | B | B | A |
| 4.5 | 20 | A | A | A | A |
| 5.4 | 20 | A | A | A | A |
| 10 | 20 | A | A | A | A |
| | 30 | A | A | A | A |
| | 40 | A | A | A | A |

From Table 3, it was confirmed that, if the LiCl concentration is 10 mass %, the solubility is stable in practical temperatures ranging from 25 to 100° C. when the protein concentration is 40 mass % or less.

Example 2

(1) Spinning Solution (Dope Solution)

The protein used in Example 1 was used to produce a spinning solution (dope solution). First, freeze-dried powder (protein) was added to DMSO (100° C.) containing 10 mass % LiCl so that the concentration of the freeze-dried powder became 20 mass %. After 6 hours of dissolution using a rotator, dusts and bubbles were removed. The viscosity of the protein solution was 1,200 cP (centipoises). Thus, the spinning solution (dope solution) was prepared.

(2) Spinning-Drawing Processes

The method shown in FIG. 2A was adopted as the spinning and drawing processes. The spinning solution was filled in a cylinder and extruded from a nozzle 0.3 mm in diameter at a speed of 2.0 ml/h using a syringe pump, and thereafter the solvent was extracted in a 100 mass % methanol coagulation liquid, so as to produce an undrawn yarn. The length of the coagulation liquid bath was 250 mm, and the take-up speed was 2.1 m/min. Next, as drawing, the undrawn yarn was drawn to 4.5 times in hot water at 50° C. The take-up speed was 9.35 m/min.

(3) Physical Property Measurement (a) The fiber diameter was measured using an optical microscope.

(b) Tensile test

The strength, the initial elastic modulus (obtained based on the measurement of inclinations of 20 points: inclinations were measured at 20 points with an interval of 50 msec and the maximum inclination was defined as the initial elastic modules), and the elongation of the fiber were measured using a tensile tester (small table-top tester EZ-S manufactured by Shimadzu Corporation) under an ambient temperature of 25° C. and a relative humidity of 60%, and the toughness was calculated. The sample was attached to a cardboard form, the distance between grippers was 20 mm, and the tensile speed was 10 mm/min. The load cell capacity was 1 N, and the gripper was a clip type. The measured value was an average of five samples (n=5). The formula for calculating toughness was as follows:

$$\text{Toughness} = [E/(r^2 \times \pi \times L) \times 1000] (\text{unit: MJ/m}^3),$$

where
 E Fracture energy (unit: J)
 r Fiber radius (unit: mm)
 π Pi
 L Distance between grippers in tensile test measurement.

Figure 5:
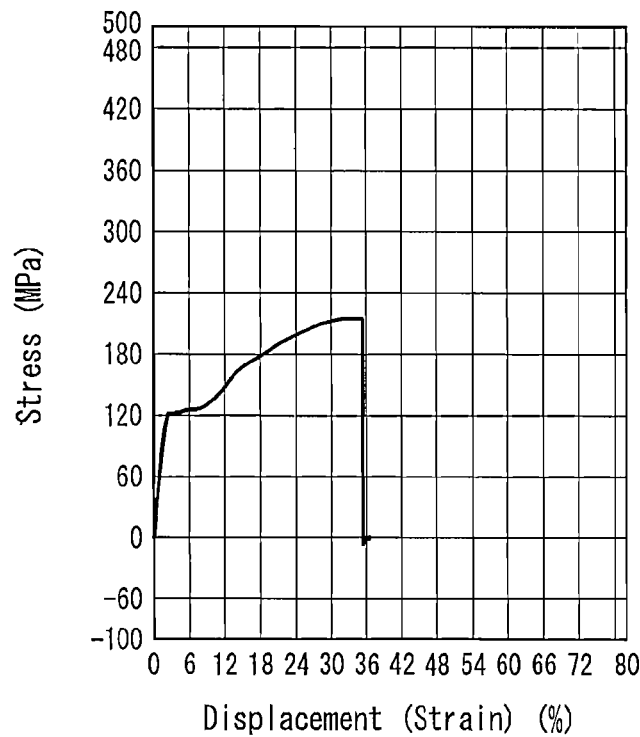
FIG. 5 is a single fiber stress-displacement (strain) curve of fibers obtained in Example 2 of the present invention.

Table 4 summaries various physical properties of the fibers. Further, FIG. 5 shows the stress-displacement (strain) curve of the obtained fiber.

Example 3

The spinning solution identical to that in Example 2 was filled in a cylinder and extruded from a nozzle 0.3 mm in diameter at a speed of 1.4 ml/h using a syringe pump, and thereafter the solvent was extracted in a 100 mass % methanol coagulation liquid, so as to produce an undrawn yarn. The length of the coagulation liquid bath was 250 mm, and the take-up speed was 2.2 m/min. Next, as drawing, the undrawn yarn was drawn to 3.5 times in hot water at 50° C. The take-up speed was 7.7 m/min. Thereafter, the yarn was drawn to 1.25 times by dry-heat drawing at 160° C. The method shown in FIGS. 2A and 2B was adopted as the spinning and drawing processes.

Figure 6:
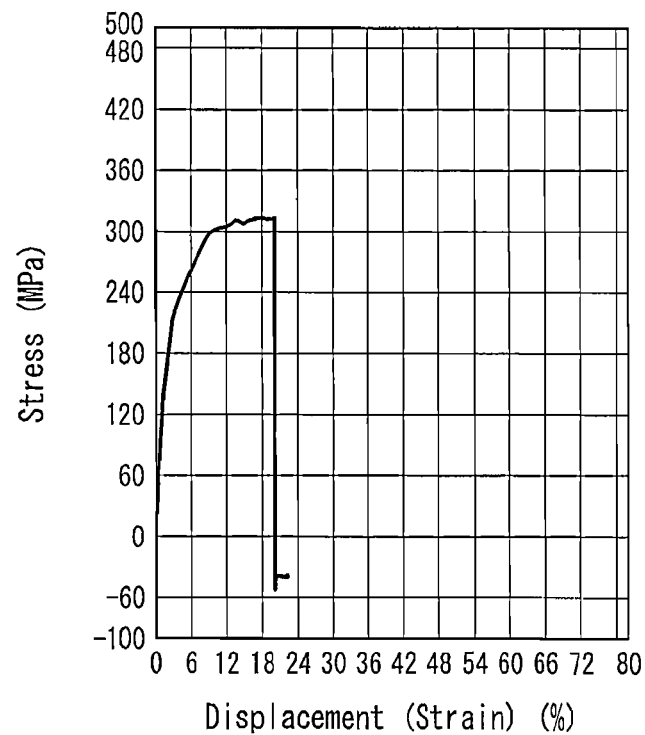
FIG. 6 is a single fiber stress-displacement (strain) curve of fibers obtained in Example 3 of the present invention.

Various physical properties of the obtained fiber were measured as described above, and Table 4 summarizes the results. FIG. 6 shows the stress-displacement (strain) curve of the obtained fiber.

TABLE 4

|  | Maximum point test force (mN) | Maximum point stress (MPa) | Initial elastic modulus (GPa) | Displacement at rupture point (%) | Diameter (mm) | Toughness (MJ/m$^3$) |
|---|---|---|---|---|---|---|
| Ex. 2 | 70.5 | 213.7 | 6.2 | 35.2 | 0.0205 | 59.1 |
| Ex. 3 | 119.1 | 313.3 | 9.4 | 19.9 | 0.0220 | 52.6 |

Example 4

The spinning solution was produced in the same manner as in Example 2 except that the protein concentration was 7 mass % and only DMSO was used as the solvent. The spinning device shown in FIGS. 2A-2B was used. The following are respective conditions in the wet spinning.

(1) Extrusion-Coagulation Processes
Diameter of extrusion nozzle: 0.3 mm
Extrusion speed: 3.0 ml/h
Temperature of coagulation liquid in the bath: 10° C.

(2) First-Stage Drawing
The first-stage drawing was performed in hot water at 50° C., at a draw ratio of 2.5 times and a take-up speed of 5.5 m/min (55 rpm) for 3.5 minutes.

(3) Second-Stage Drawing
The second-stage drawing was performed in a dry-heating furnace at 190° C., at a feeding speed of 20 rpm and a take-up speed of 31 rpm (draw ratio: 1.55 times).

Figure 7:
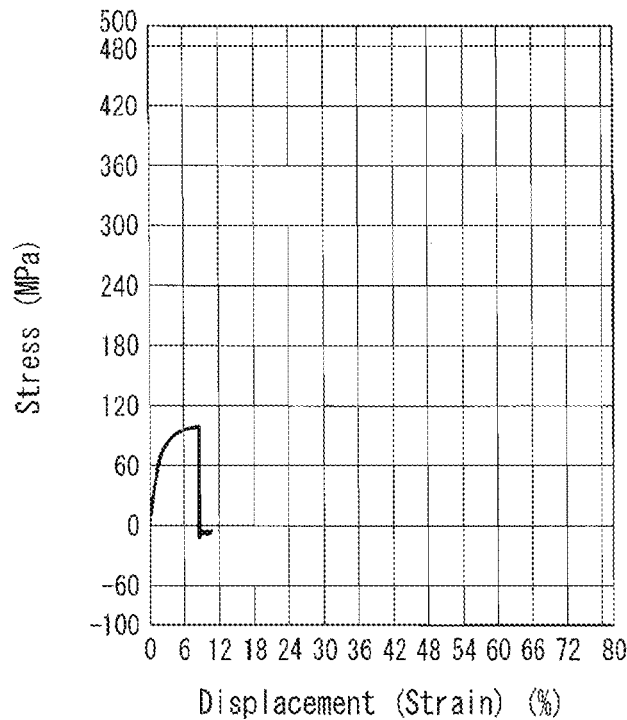
FIG. 7 is a single fiber stress-displacement (strain) curve of fibers obtained in Example 4 of the present invention.

(4) Physical Properties of the Obtained Drawn Yarn
The physical properties of the obtained drawn yarn were measured as described above. As a result, the average diameter of the single fiber was 22.0 μm, the maximum point stress was 99.2 MPa, the initial elastic modulus was 3.5 GPa, the displacement at rupture point (elongation) was 8.7%, and the toughness was 6.8 MJ/m$^3$. FIG. 7 shows the single fiber stress-displacement (strain) curve of the obtained fibers.

Example 5

The spinning solution was produced in the same manner as in Example 2 except that the protein concentration was 10 mass % and only DMSO was used as the solvent. In the case where the solvent does not contain a dissolution promoter such as an inorganic salt, a high concentration of protein results in gelation. Because of this, the syringe 31 shown in FIG. 2A was heated at 60° C. using a heater and spinning was performed while avoiding gelation of the solution. The spinning device shown in FIGS. 2A-2B was used for the wet spinning-drawing. The following are respective conditions in the wet spinning.

(1) Extrusion-Coagulation Processes
Temperature of syringe heater: 60° C.
Diameter of extrusion nozzle: 0.2 mm
Extrusion speed: 4.0 ml/h
Temperature of coagulation liquid in the bath: 10° C.

(2) First-Stage Drawing
The first-stage drawing was performed in hot water at 50° C., at a draw ratio of 3.5 times and a take-up speed of 7.7 m/min (77 rpm) for 4 minutes.

(3) Second-Stage Drawing
The second-stage drawing was performed in a dry-heating furnace at 180° C., at a feeding speed of 20 rpm and a take-up speed of 26 rpm (draw ratio: 1.3 times).

Figure 8:
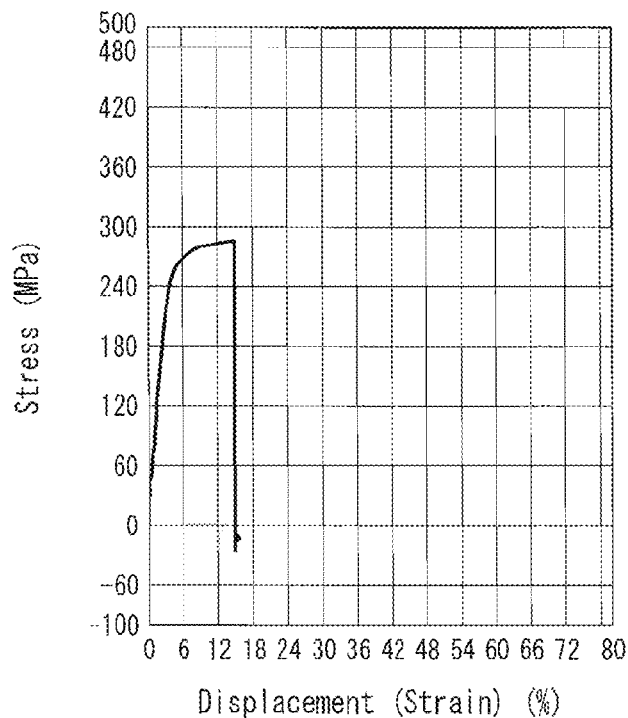
FIG. 8 is a single fiber stress-displacement (strain) curve of fibers obtained in Example 5 of the present invention.

(4) Physical Properties of the Obtained Drawn Yarn
The physical properties of the obtained drawn yarn were measured as described above. As a result, the average diameter of the single fiber was 22.0 μm, the maximum point stress was 285.9 MPa, the initial elastic modulus was 7.6 GPa, the displacement at rupture point (elongation) was 14.8%, and the toughness was 35.5 MJ/m$^3$. FIG. 8 shows the single fiber stress-displacement (strain) curve of the obtained fibers.

Example 6

(1) Used Protein
(I) About 4.5 g of bacteria cells of the *Escherichia coli* expressing the ADF4Kai protein and 30 ml of a buffer solution AI (20 mM Tris-HCl, pH 7.4) were added to a centrifuge tube (50 ml). After dispersing the bacteria cells with a mixer ("SI-0286" manufactured by GE, level 10), the dispersion was centrifuged (10,000 rpm, 10 minutes, room temperature) with a centrifuge ("MX-305" manufactured by TOMY SEIKO Co., Ltd.), and a supernatant was discarded.

(II) To a precipitate (bacteria cells) obtained by the centrifugation, 30 ml of the buffer solution AI and 0.3 ml of 0.1 M PMSF (dissolved by isopropanol) were added. After dispersing the precipitate for 3 minutes with the above-described mixer (level 10) manufactured by GE, the bacteria cells were disrupted using an ultrasonic disrupter ("VCX500" manufactured by Sonics & Materials, Inc.) and centrifuged (10,000 rpm, 10 minutes, room temperature).

(III) To a precipitate (insoluble fraction protein) obtained by the centrifugation, 30 mL of a buffer solution B (50 mM Tris-HCl, 100 mM NaCl, pH 7.0) containing 3 w/v % of SDS was added. After dispersing the precipitate for 3 minutes with a mixer ("T18 basic ULTRA TURRAX" manufactured by IKA, level 2), the dispersion was stirred for 60 minutes with a shaker (bioshaker "BR-43FL" manufactured by TAITEC CORPORATION, 200 rpm, 37° C.). Thereafter, the stirred dispersion was centrifuged (10,000 rpm, 10 minutes, room temperature) with the above-described centrifuge manufactured by TOMY SEIKO Co., Ltd., and a supernatant was removed.

(IV) The precipitate from which the supernatant had been removed was dissolved with DMSO (containing 2M LiCl) at 80° C., stirred by a stirrer, centrifuged (11,000×g, 10 minutes, room temperature) with the above-described centrifuge manufactured by TOMY SEIKO Co., Ltd., and a supernatant was dialyzed with water using a dialysis tube (cellulose tube 36/32 manufactured by Sanko Junyaku Co., Ltd.). Aggregate protein (white) obtained after dialysis was collected by centrifugation, and water was removed by a freeze dryer, so as to collect freeze-dried powder. The purification degree of the target protein ADF4Kai (about 37.7 kDa) in the obtained freeze-dried powder was checked by analyzing images of the results of polyacrylamide gel electrophoresis (Oriole staining by Oriole Fluorescent Gel Stain manufacture by Bio-RAD Laboratories, Inc.) of said protein powder using ImageLab (Bio-RAD Laboratories, Inc.). As a result, the purification degree of ADF4Kai was about 75.5%.

(2) Spinning Solution (Dope Solution)
The spinning solution was produced using the ADF4Kai protein obtained above. Freeze-dried powder was added to DMSO that had been heated at 80° C. so that the concentration of the freeze-dried powder became 10.2 mass %. After 6 hours of dissolution using a rotator, dusts and bubbles were removed. The viscosity of the protein solution was 1,200 cP (centipoises). This was used as the spinning solution.

(3) Spinning-Drawing Processes

The wet spinning was preformed using the spinning solution obtained above. The spinning device shown in FIG. 4A was used for the extrusion-coagulation processes. The following are respective conditions in the wet spinning.

(I) Extrusion-Coagulation Processes
Diameter of extrusion nozzle: 0.3 mm
Extrusion speed: 6.0 ml/h
Temperature of coagulation liquid in the bath: 4° C.
Take-up speed: 13.6 m/min (II) First-Stage Drawing
The first-stage drawing was performed in hot water at 50° C., at a draw ratio of 1.5 times.

(III) Second-Stage Drawing
The second-stage drawing was performed in a dry-heating furnace at 180° C., at a draw ratio of 1.3 times.

Figure 9:
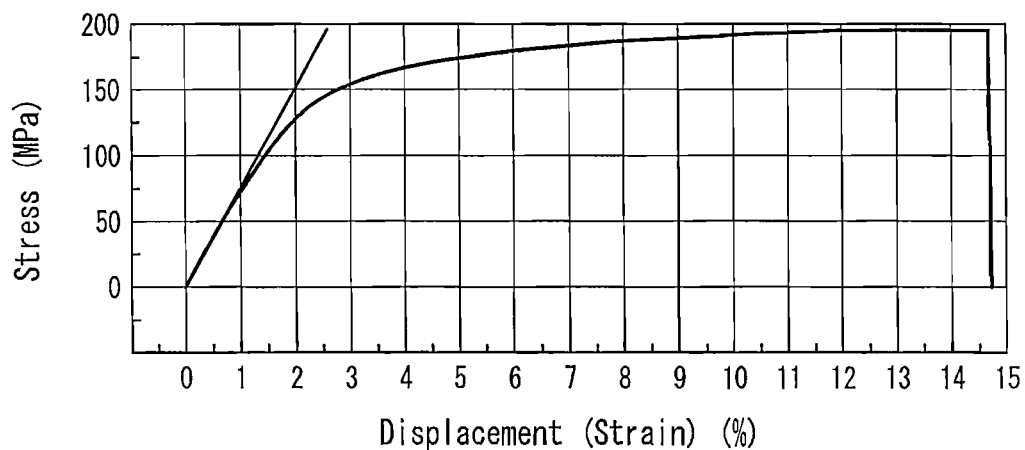
FIG. 9 is a stress-displacement (strain) curve of a drawn yarn obtained in Example 6 of the present invention.

(IV) Physical Properties of the Obtained Drawn Yarn
The physical properties of the obtained drawn yarn were measured as described above. As a result, the average diameter of the single fiber was 83.8 μm, the maximum point stress was 196.4 MPa, the initial elastic modulus was 6.0 GPa, the displacement at rupture point (elongation) was 14.6%, and the toughness was 24.6 MJ/m$^3$. FIG. 9 shows the single fiber stress-displacement (strain) curve of the obtained fibers.

Example 7

(1) Used Protein (I) About 4.5 g of bacteria cells of the *Escherichia coli* expressing the MaSp2_N protein and 30 ml of a buffer solution AI (20 mM Tris-HCl, pH 7.4) were added to a centrifuge tube (50 ml). After dispersing the bacteria cells with a mixer ("SI-0286" manufactured by GE, level 10), the dispersion was centrifuged (10,000 rpm, 10 minutes, room temperature) with a centrifuge ("MX-305" manufactured by TOMY SEIKO Co., Ltd.), and a supernatant was discarded.

(II) To a precipitate (bacteria cells) obtained by the centrifugation, 30 ml of the buffer solution AI and 0.3 ml of 0.1 M PMSF (dissolved by isopropanol) were added. After dispersing the precipitate for 3 minutes with the above-described mixer (level 10) manufactured by GE, the bacteria cells were disrupted using an ultrasonic disrupter ("VCX500" manufactured by Sonics & Materials, Inc.) and centrifuged (10,000 rpm, 10 minutes, room temperature).

(III) To a precipitate (insoluble fraction protein) obtained by the centrifugation, 30 mL of a buffer solution B (50 mM Tris-HCl, 100 mM NaCl, pH 7.0) containing 3 w/v % of SDS was added. After dispersing the precipitate for 3 minutes with a mixer ("T18 basic ULTRA TURRAX" manufactured by IKA, level 2), the dispersion was stirred for 60 minutes with a shaker (bioshaker "BR-43FL" manufactured by TAITEC CORPORATION, 200 rpm, 37° C.). Thereafter, the stirred dispersion was centrifuged (10,000 rpm, 10 minutes, room temperature) with the above-described centrifuge manufactured by TOMY SEIKO Co., Ltd., and a supernatant was removed.

(IV) The precipitate, from which the supernatant had been removed, was dissolved with DMSO (containing 2M LiCl) at 80° C., stirred by a stirrer, centrifuged (11,000×g, 10 minutes, room temperature) with the above-described centrifuge manufactured by TOMY SEIKO Co., Ltd., and the obtained supernatant was dialyzed with water using a dialysis tube (cellulose tube 36/32 manufactured by Sanko Junyaku Co., Ltd.). Aggregate protein (white) obtained after dialysis was collected by centrifugation, and water was removed by a freeze dryer, so as to collect freeze-dried powder. The purification degree of the target protein MaSp2_N (about 31.7 kDa) in the obtained freeze-dried powder was checked by analyzing images of the results of polyacrylamide gel electrophoresis (Oriole staining) of said protein powder using ImageLab (Bio-RAD Laboratories, Inc.). As a result, the purification degree of MaSp2_N was about 68.1%.

(2) Spinning Solution (Dope Solution)

The spinning solution was produced using the MaSp2_N protein obtained above. Freeze-dried powder was added to DMSO that had been heated at 40° C. so that the concentration of the freeze-dried powder became 18 mass %. After 6 hours of dissolution using a rotator, dusts and bubbles were removed. The viscosity of the protein solution was 1,200 cP (centipoises). This was used as the spinning solution.

(3) Spinning-Drawing Processes

The wet spinning was preformed using the spinning solution obtained above. The spinning device shown in FIG. 4A was used for the extrusion-coagulation processes. The following are respective conditions in the wet spinning.

(I) Extrusion-Coagulation Processes
Diameter of extrusion nozzle: 0.2 mm
Extrusion speed: 2.0 ml/h
Temperature of coagulation liquid in the bath: 10° C.
Take-up speed: 2.5 m/min (II) First-Stage Drawing
The first-stage drawing was performed in hot water at 50° C., at a draw ratio of 2.5 times.

(III) Second-Stage Drawing
The second-stage drawing was performed in a dry-heating furnace at 80° C., at a draw ratio of 1.85 times.

Figure 10:
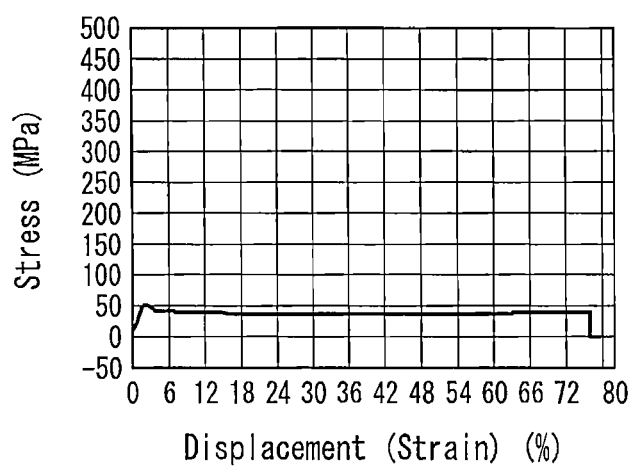
FIG. 10 is a single fiber stress-displacement (strain) curve of fibers obtained in Example 7 of the present invention.

(IV) Physical Properties of the Obtained Drawn Yarn
The physical properties of the obtained drawn yarn were measured as described above. As a result, the average diameter of the single fiber was 35 μm, the maximum point stress was 236.7 MPa, the initial elastic modulus was 5.7 GPa, the displacement at rupture point (elongation) was 14.9%, and the toughness was 26.5 MJ/m$^3$. FIG. 10 shows the single fiber stress-displacement (strain) curve of the obtained fibers.

Example 8

(1) Used Protein (I) About 4.5 g of bacteria cells of the *Escherichia coli* expressing the Flag__92_short2 protein and 30 ml of a buffer solution AI (20 mM Tris-HCl, pH 7.4) were added to a centrifuge tube (50 ml). After dispersing the bacteria cells with a mixer ("SI-0286" manufactured by GE, level 10), the dispersion was centrifuged (10,000 rpm, 10 minutes, room temperature) with a centrifuge ("MX-305" manufactured by TOMY SEIKO Co., Ltd.), and a supernatant was discarded.

(II) To a precipitate (bacteria cells) obtained by the centrifugation, 30 ml of the buffer solution AI and 0.3 ml of 0.1 M PMSF (dissolved by isopropanol) were added. After dispersing the precipitate for 3 minutes with the above-described mixer (level 10) manufactured by GE, the bacteria cells were disrupted using an ultrasonic disrupter ("VCX500" manufactured by Sonics & Materials, Inc.). The ultrasonic disruption was performed by repeating a 20-second processing and a 5-second pause for 8 minutes in total.

(III) The bacteria cells after ultrasonic disruption were centrifuged (11,000×g, 30 minutes, room temperature) with a centrifuge ("MX-305" manufactured by TOMY SEIKO Co., Ltd.).

(IV) To a supernatant (soluble fraction protein) obtained by the centrifugation, Ni sepharose (50% slurry, manufactured by GE Healthcare Japan Corporation, product number "17-5318-02") was added. After dispersing the mixture for 3 minutes with a mixer ("T18 basic ULTRA TURRAX" manufactured by IKA, level 2), the dispersion was stirred for 60 minutes with a stirrer. Thereafter, the stirred dispersion was centrifuged (500×g, 5 minutes, room temperature) with the above-described centrifuge manufactured by TOMY SEIKO Co., Ltd., and a supernatant was removed. The Ni sepharose was filled in an empty column (manufactured by GE Healthcare Japan Corporation, product number "17-0435-01") and washed with the buffer solution AI, and thereafter the Flag_92_short2 protein was eluted using an elution buffer (50 mM Tris, 50 mM NaCl, 300 mM imidazole, pH 7.5).

(V) The obtained eluate was dialyzed with water using a dialysis tube (cellulose tube 36/32 manufactured by Sanko Junyaku Co., Ltd.). The moisture of the liquid obtained after dialysis was removed using a freeze dryer, so as to collect freeze-dried powder. The purification degree of the target protein Flag_92_short2 (about 46.6 kDa) in the obtained freeze-dried powder was checked by analyzing images of the results of polyacrylamide gel electrophoresis (Oriole staining) of said protein powder using ImageLab (Bio-RAD Laboratories, Inc.). As a result, the purification degree of Flag_92_short2 was about 69.1%.

(2) Spinning Solution (Dope Solution)

The spinning solution was produced using the Flag_92_short2 protein obtained above. Freeze-dried powder was added to DMSO that had been heated at 45° C. so that the concentration of the freeze-dried powder became 23 mass %. After 6 hours of dissolution using a rotator, dusts and bubbles were removed. The viscosity of the protein solution was 1,200 cP (centipoises). This was used as the spinning solution.

(3) Spinning-Drawing Processes

The wet spinning was preformed using the spinning solution obtained above. The spinning device shown in FIG. 4A was used for the extrusion-coagulation processes. The following are respective conditions in the wet spinning.

(I) Extrusion-Coagulation Processes

Diameter of extrusion nozzle: 0.2 mm

Extrusion speed: 1.0 ml/h

Temperature of coagulation liquid in the bath: 10° C.

Take-up speed: 1.65 m/min (II) First-Stage Drawing

The first-stage drawing was performed in air at room temperature at a draw ratio of 1.5 times. The fiber obtained in this stage is referred to as a primary drawn yarn.

(III) Second-Stage Drawing

The second-stage drawing was performed in a dry-heating furnace at 160° C. at a draw ratio of 1.34 times. The fiber obtained in this stage is referred to as a secondary drawn yarn.

(IV) Physical Properties of the Obtained Drawn Yarns

Figure 11:
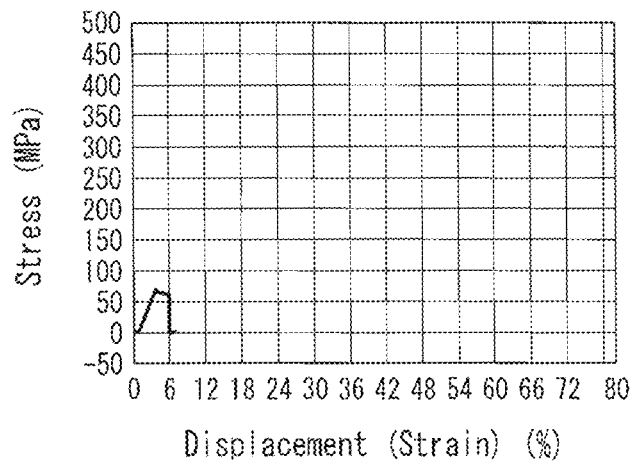
FIG. 11 is a single fiber stress-displacement (strain) curve of fibers in a primary drawn yarn obtained in Example 8 of the present invention.
Figure 12:
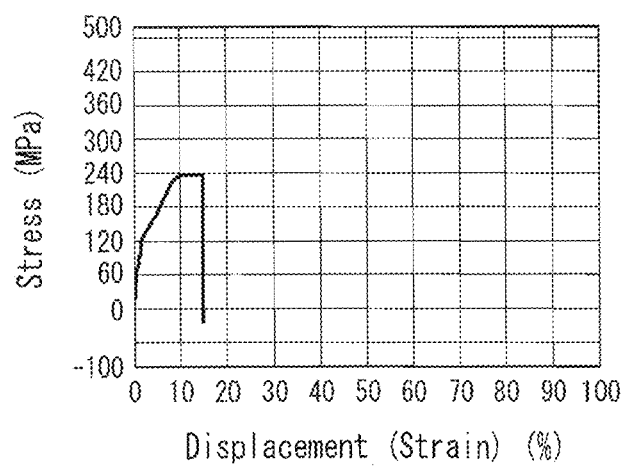
FIG. 12 is a single fiber stress-displacement (strain) curve of fibers in a secondary drawn yarn obtained in Example 8 of the present invention.

The physical properties of the obtained primary drawn yarn and the secondary drawn yarn were measured as described above. Table 5 below shows the results. Further, FIGS. 11 and 12 show the single fiber stress-displacement (strain) curves of fibers of the obtained primary drawn yarn and secondary drawn yarn, respectively.

TABLE 5

| | Maximum point stress (MPa) | Initial elastic modulus (GPa) | Displacement at rupture point (%) | Diameter (μm) | Toughness (MJ/m$^3$) |
|---|---|---|---|---|---|
| Primary drawn yarn | 48.9 | 2.3 | 75.9 | 68.7 | 26.7 |
| Secondary drawn yarn | 67.6 | 0.02 | 14.6 | 52.0 | 0.2 |

Example 9

<Protein Extraction>

(1) About 4.5 g of bacteria cells of the *Escherichia coli* expressing the ADF3Kai-Large-NRSH1 protein and 30 ml of a buffer solution AI (20 mM Tris-HCl, pH 7.4) were added to a centrifuge tube (50 ml). After dispersing the bacteria cells with a mixer ("SI-0286" manufactured by GE, level 10), the dispersion was centrifuged (10,000 rpm, 10 minutes, room temperature) with a centrifuge ("MX-305" manufactured by TOMY SEIKO Co., Ltd.), and a supernatant was discarded.

(2) To a precipitate (bacteria cells) obtained by the centrifugation, 30 ml of the buffer solution AI and 0.3 ml of 0.1 M PMSF (dissolved by isopropanol) were added. After dispersing the precipitate for 3 minutes with the above-described mixer (level 10) manufactured by GE, the bacteria cells were disrupted using an ultrasonic disrupter ("VCX500" manufactured by Sonics & Materials, Inc.) and centrifuged (10,000 rpm, 10 minutes, room temperature). After discarding a supernatant, it was left for about 10 minutes in ice water to lower the temperature. The same bacteria cell disruption and centrifugation were repeated again.

<Protein Washing>

To a precipitate (insoluble fraction protein) obtained by the centrifugation, 30 mL of a buffer solution B (50 mM Tris-HCl, 100 mM NaCl, pH 7.0) containing 3 w/v % of SDS was added. After dispersing well the precipitate with the above-described ultrasonic disrupter (level 7) manufactured by SMT, the dispersion was stirred for 60 minutes with a shaker (manufactured by TAITEC CORPORATION, 200 rpm, 37° C.). Thereafter, the stirred dispersion was centrifuged (10,000 rpm, 10 minutes, room temperature) with the above-described centrifuge manufactured by TOMY SEIKO Co., Ltd., and a supernatant was discarded, whereby SDS washing granules (precipitate) were obtained.

<Protein Purification>

The SDS washing granules were suspended in each solvent shown in Table 6 below so that the concentration of the SDS washing granules became 100 mg/mL, and the suspension was subjected to heat treatment at 80° C. for one hour. Thereafter, the suspension after heat treatment was centrifuged (11000×g, 5 minutes) with the above-described centrifuge manufactured by TOMY SEIKO Co., Ltd., and a supernatant was collected. The concentration of the protein in the supernatant was measured by a BCA method. Incidentally, for the measurement of protein by the BCA method, Pierce (trademark) BCA Protein Assay Kit manufactured by TAKARA BIO INC. was used.

Example 10

The ADF4Kai protein was purified in the same manner as in Example 9, except that the *Escherichia coli* expressing the ADF4Kai protein was used instead of the *Escherichia coli* expressing the ADF3Kai-Large-NRSH1 protein.

Figure 13:
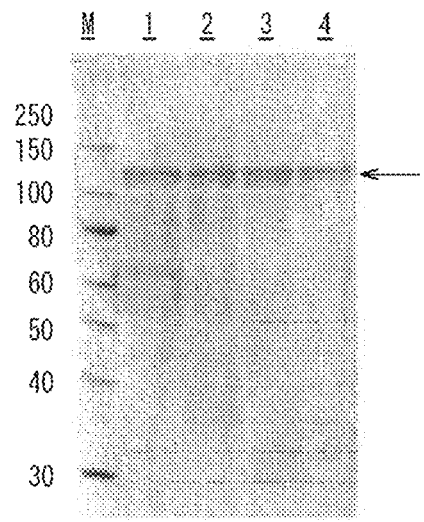
FIG. 13 is a photograph showing a result of SDS-PAGE electrophoresis of a protein obtained in Example 9 of the present invention.
Figure 14:
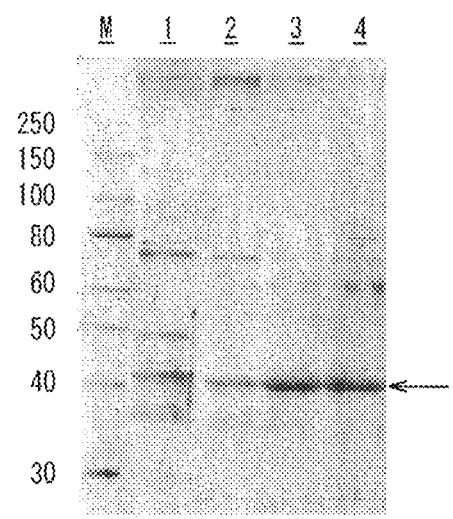
FIG. 14 is a photograph showing a result of SDS-PAGE electrophoresis of a protein obtained in Example 10 of the present invention.

The proteins obtained in Examples 9-10 were subjected to SDS-PAGE electrophoresis. Their bands were checked by Oriole staining, and images were analyzed using an analysis software Image Lab (Bio-RAD Laboratories, Inc.), so as to calculate the purity (purification degree) of the target proteins. The table 6 below shows the results. Incidentally, FIG. 13 shows the result of the SDS-PAGE electrophoresis of the protein (including ADF3Kai-Large-NRSH1) obtained in Example 9, and FIG. 14 shows the result of the SDS-PAGE electrophoresis of the protein (including ADF4Kai) obtained in Example 10. Further, Table 6 below shows relative values based on the purity of protein in the case of using a 7.5 M urea buffer solution (pH 9.0) as a solvent.

TABLE 6

|  | Protein | | | |
|---|---|---|---|---|
|  | ADF3Kai-Large-NRSH1 | | ADF4Kai | |
| Solvent | Purification degree (%) | Purity index | Purification degree (%) | Purity index |
| 7.5M urea buffer solution (pH 9.0) | 35.18 | 1 | 32.67 | 1 |
| DMSO (containing 1M LiCl) | 44.39 | 1.26 | 60.02 | 1.84 |
| DMSO (containing 2M LiCl) | 42.85 | 1.22 | 75.55 | 2.31 |
| DMSO (containing 3M LiCl) | 51.53 | 1.46 | 76.38 | 2.34 |

FIG. 13 shows the results of the electrophoresis (SDS-PAGE) using the polypeptide solutions in which the ADF3Kai-Large-NRSH1 protein was dissolved in various solvents, and FIG. 14 shows the results of the electrophoresis (SDS-PAGE) using the polypeptide solutions in which the ADF4Kai protein was dissolved in various solvents. In FIGS. 13 and 14, a lane M indicates a molecular-weight marker, and lanes 1-4 respectively indicate protein samples using a 7.5 M urea buffer solution (pH 9.0), DMSO (containing 1M LiCl), DMSO (containing 2M LiCl), and DMSO (containing 3M LiCl) as solvents. As is apparent from FIGS. 13 and 14, the case of using DMSO with an inorganic salt as a solvent contained less impure proteins and improved its solubility as compared with the case of using the 7.5 M urea buffer solution (pH 9.0) as a solvent. Further, the purification degree improved with an increase in the concentration of the inorganic salt in the solvent.

INDUSTRIAL APPLICABILITY

The polypeptide solution of the present invention can be used as a dope solution and for polypeptide purification. Further, the artificial polypeptide fibers produced using the polypeptide solution of the present invention as a dope solution can be used suitably as reinforcing fibers of resin and metal, composite materials, and for injection molding, etc. The uses can be applied to transport device members such as cars, reinforcing fibers of tires, etc. Moreover, the artificial polypeptide fibers of the present invention can be applied to surgical threads, masks, filters, wound covering materials, regenerative medicine sheets, biosheets, etc. They can be in the form of weaves, knits, braids, nonwoven fabrics, etc.

DESCRIPTION OF REFERENCE NUMERALS 1, 31, 61, 81 extruder
2, 30, 62, 80 undrawn-yarn production device
3, 40 wet-heat drawing device (first-stage drawing device)
4, 50, 63, 90 dry-heat drawing device (second-stage drawing device)
5, 39, 44, 64, 86, 92 yarn roll
6, 32, 66, 82 spinning solution
7 storage tank
8 gear pump
9, 69, 83 spinneret
10, 60 spinning-drawing device
11, 35, 71, 85 coagulation liquid
36 undrawn yarn
12, 38 hot water
13, 15, 41, 45 supply nip roller
14, 16, 42, 46 take-up nip roller
17, 43, 77, 89 dry-heat drawing device
18a-18f yarn guide
19, 73 air gap
20, 34, 72, 84 coagulation liquid bath
21, 37 drawing bath
22, 47, 78, 91 guide

SEQUENCE LISTING FREE TEXT

SEQ ID NOS: 1-6, 8, 15, 17, 19 amino acid sequence
SEQ ID NOS: 7, 9, 10, 16, 18, 20 base sequence
SEQ ID NOS: 11-14 primer sequence

The invention claimed is:

1. A polypeptide solution in which a polypeptide derived from natural spider silk proteins is dissolved in a solvent,
wherein the solvent contains at least one selected from the following (i)-(iii):
   (i) Dimethyl sulfoxide;
   (ii) Dimethyl sulfoxide with an inorganic salt; and
   (iii) N, N-dimethylformamide with an inorganic salt.

2. The polypeptide solution according to claim 1, wherein, when the polypeptide solution is 100 mass %, the percentage of the polypeptide is in a range of 3 to 45 mass %.

3. The polypeptide solution according to claim 1, wherein, when the solvent is 100 mass %, the percentage of the inorganic salt is in a range of 0.1 to 20 mass %.

4. The polypeptide solution according to claim 1, wherein, when the solvent is 100 mass %, the percentage of the at least one substance selected from (i)-(iii) above is 22 mass % or more and 100 mass % or less, and a remainder contains alcohol.

5. The polypeptide solution according to claim 1, wherein, when the solvent is 100 mass %, the percentage of the at least one substance selected from (i)-(iii) above is 10 mass % or more and 100 mass % or less, and a remainder contains water.

6. The polypeptide solution according to claim 1, wherein the inorganic salt is at least one selected from alkali metal halides, alkaline-earth metal halides, alkaline-earth metal nitrate, and thiocyanate.

7. The polypeptide solution according to claim 1, wherein the polypeptide solution is a dope solution.

8. A method for producing an artificial polypeptide fiber using the polypeptide solution according to claim 1, comprising:
   using the polypeptide solution as a dope solution; and
   extruding the dope solution from a spinneret into a coagulation liquid in a desolvation bath so as to eliminate a solvent from the dope solution and form a fiber to prepare an undrawn yarn, thereby obtaining an artificial polypeptide fiber.

9. The method for producing an artificial polypeptide fiber according to claim 8, further comprising:
   drawing the undrawn yarn.

10. The method for producing an artificial polypeptide fiber according to claim 8,
wherein, when the polypeptide solution is 100 mass %, the percentage of the polypeptide is in a range of 3 to 45 mass %.

11. The method for producing an artificial polypeptide fiber according to claim 8, wherein, when the solvent is 100 mass %, the percentage of the inorganic salt is in a range of 0.1 to 20 mass %.

12. A method for purifying a polypeptide using the polypeptide solution according to claim 1, comprising:
   subjecting the polypeptide solution to heat treatment and thereafter removing an undissolved substance therefrom.

13. The method for purifying a polypeptide according to claim 12, wherein the polypeptide derived from natural spider silk proteins is insoluble.

14. The method for purifying a polypeptide according to claim 12, wherein the heat treatment is performed at 45 to 100° C.

15. The method for purifying a polypeptide according to claim 12, wherein the undissolved substance is removed by separation through filtration or centrifugation.

16. The method for purifying a polypeptide according to claim 12, wherein, when the polypeptide solution is 100 mass %, the percentage of the polypeptide is in a range of 3 to 45 mass %.

17. The method for purifying a polypeptide according to claim 12, wherein, when the solvent is 100 mass %, the percentage of the inorganic salt is in a range of 0.1 to 20 mass %.

* * * * *

SEQUENCE LISTING

```
<160> NUMBER OF SEQ ID NOS: 20

<210> SEQ ID NO 1
<211> LENGTH: 50
<212> TYPE: PRT
<213> ORGANISM: Araneus diadematus

<400> SEQUENCE: 1

Ser Gly Cys Asp Val Leu Val Gln Ala Leu Leu Glu Val Val Ser Ala
1               5                   10                  15

Leu Val Ser Ile Leu Gly Ser Ser Ile Gly Gln Ile Asn Tyr Gly
            20                  25                  30

Ala Ser Ala Gln Tyr Thr Gln Met Val Gly Gln Ser Val Ala Gln Ala
        35                  40                  45
```

Leu Ala
    50

<210> SEQ ID NO 2
<211> LENGTH: 30
<212> TYPE: PRT
<213> ORGANISM: Araneus diadematus

<400> SEQUENCE: 2

Ser Gly Cys Asp Val Leu Val Gln Ala Leu Leu Glu Val Val Ser Ala
1               5                   10                  15

Leu Val Ser Ile Leu Gly Ser Ser Ile Gly Gln Ile Asn
            20                  25                  30

<210> SEQ ID NO 3
<211> LENGTH: 21
<212> TYPE: PRT
<213> ORGANISM: Araneus diadematus

<400> SEQUENCE: 3

Ser Gly Cys Asp Val Leu Val Gln Ala Leu Leu Glu Val Val Ser Ala
1               5                   10                  15

Leu Val Ser Ile Leu
            20

<210> SEQ ID NO 4
<211> LENGTH: 1183
<212> TYPE: PRT
<213> ORGANISM: Artificial
<220> FEATURE:
<223> OTHER INFORMATION: recombinant spider silk protein ADF3Kai-Large

<400> SEQUENCE: 4

Met His His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala Ala
            115                 120                 125

Ala Gly Gly Asn Gly Pro Gly Ser Gly Gln Gln Gly Ala Gly Gln Gln
        130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gln Gly Pro Gly Gln
            195                 200                 205

Gly Pro Gly Gln Gly Pro Tyr Gly Pro Gly Ala Ser Ala Ala Ala
            210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gly Pro Tyr Gly
                245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
        275                 280                 285

Tyr Gly Pro Gly Ala Ser Ala Ser Ala Ala Ser Gly Gly Tyr Gly
        290                 295                 300

Pro Gly Ser Gly Gln Gln Gly Pro Gly Gln Gln Gly Pro Gly Gln
305                 310                 315                 320

Gly Pro Tyr Gly Pro Gly Ala Ser Ala Ala Ala Ala Ala Gly Gly
                325                 330                 335

Tyr Gly Pro Gly Ser Gly Gln Gln Gly Pro Gly Gln Gln Gly Pro Gly
                340                 345                 350

Gln Gln Gly Pro Gly Gln Gln Gly Pro Gly Gln Gly Pro Tyr Gly
                355                 360                 365

Pro Gly Ala Ser Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
                420                 425                 430

Gln Gly Ala Tyr Gly Pro Gly Ala Ser Ala Ala Gly Ala Ala Gly
            435                 440                 445

Gly Tyr Gly Pro Gly Ser Gly Gln Gln Gly Pro Gly Gln Gln Gly Pro
    450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
        515                 520                 525

Gly Gly Gln Gly Pro Tyr Gly Pro Gly Ala Ala Ser Ala Ala Val Ser
        530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
                565                 570                 575

Ala Ser Ala Ala Ala Ala Ala Gly Gly Tyr Gly Pro Gly Ser Gly
            580                 585                 590

Gln Gln Gly Pro Ser Gln Gly Pro Gly Gln Gly Pro Gly Gly
        595                 600                 605

Gln Gly Pro Tyr Gly Pro Gly Ala Ser Ala Ala Ala Ala Ala Gly
            610                 615                 620

-continued

Gly Tyr Gly Pro Gly Ser Gly Gln Gln Gly Gly Gln Gly Pro
625                 630                 635                 640

Tyr Gly Pro Gly Ser Ser Ala Ala Ala Ala Ala Gly Gly Asn Gly
            645                 650                     655

Pro Gly Ser Gly Gln Gly Ala Gly Gln Gln Gly Pro Gly Gln Gln
                660                 665                 670

Gly Pro Gly Ala Ser Ala Ala Ala Ala Gly Gly Tyr Gly Pro
        675                 680                 685

Gly Ser Gly Gln Gln Gly Pro Gly Gln Gln Gly Pro Gly Gln Gly
    690                 695                 700

Pro Tyr Gly Pro Gly Ala Ser Ala Ala Ala Ala Ala Gly Gly Tyr
705                 710                 715                 720

Gly Pro Gly Ser Gly Gln Gly Pro Gly Gln Gln Gly Pro Gly Gln
                725                 730                 735

Gly Pro Tyr Gly Pro Gly Ala Ser Ala Ala Ala Ala Ala Gly Gly
            740                 745                 750

Tyr Gly Pro Gly Ser Gly Gln Gln Gly Pro Gly Gln Gln Gly Pro
                755                 760                 765

Gln Gln Gly Pro Gly Gly Gln Gly Pro Tyr Gly Pro Gly Ala Ser Ala
770                 775                 780

Ala Ala Ala Ala Gly Gly Tyr Gly Pro Gly Tyr Gly Gln Gln Gly
785                 790                 795                 800

Pro Gly Gln Gln Gly Pro Gly Gly Gln Gly Pro Tyr Gly Pro Gly Ala
                805                 810                 815

Ser Ala Ala Ser Ala Ala Ser Gly Gly Tyr Gly Pro Gly Ser Gly Gln
        820                 825                 830

Gln Gly Pro Gly Gln Gln Gly Pro Gly Gly Gln Gly Pro Tyr Gly Pro
            835                 840                 845

Gly Ala Ser Ala Ala Ala Ala Ala Gly Gly Tyr Gly Pro Gly Ser
850                 855                 860

Gly Gln Gln Gly Pro Gly Gln Gln Gly Pro Gly Gln Gln Gly Pro Gly
865                 870                 875                 880

Gln Gln Gly Pro Gly Gly Gln Gly Pro Tyr Gly Pro Gly Ala Ser Ala
            885                 890                 895

Ala Ala Ala Ala Gly Gly Tyr Gly Pro Gly Ser Gly Gln Gln Gly
            900                 905                 910

Pro Gly Gln Gln Gly Pro Gly Gln Gln Gly Pro Gly Gln Gln Gly Pro
            915                 920                 925

Gly Gln Gln Gly Pro Gly Gln Gln Gly Pro Gly Gln Gln Gly Pro Gly
930                 935                 940

Gln Gln Gly Pro Gly Gln Gln Gly Pro Gly Gln Gln Gly Ala Tyr Gly
945                 950                 955                 960

Pro Gly Ala Ser Ala Ala Ala Gly Ala Ala Gly Gly Tyr Gly Pro Gly
            965                 970                 975

Ser Gly Gln Gln Gly Pro Gly Gln Gln Gly Pro Gly Gln Gln Gly Pro
    980                 985                 990

Gly Gln Gln Gly Pro Gly Gln Gln Gly Pro Gly Gln Gln Gly Pro Gly
    995                 1000                1005

Gln Gln Gly Pro Gly Gln Gln Gly Pro Tyr Gly Pro Gly Ala Ser
    1010                1015                1020

Ala Ala Ala Ala Ala Ala Gly Gly Tyr Gly Pro Gly Ser Gly Gln
    1025                1030                1035

Gln Gly Pro Gly Gln Gln Gly Pro Gly Gln Gln Gly Pro Gly Gly

```
           1040                1045                1050

Gln Gly  Pro Tyr Gly  Pro Gly  Ala Ala Ser  Ala Ala  Val Ser Val
    1055                1060                1065

Gly Gly  Tyr Gly Pro  Gln Ser  Ser Ser Val  Pro Val  Ala Ser Ala
    1070                1075                1080

Val Ala  Ser Arg Leu  Ser Ser  Pro Ala Ala  Ser Ser  Arg Val Ser
    1085                1090                1095

Ser Ala  Val Ser Ser  Leu Val  Ser Ser Gly  Pro Thr  Lys His Ala
    1100                1105                1110

Ala Leu  Ser Asn Thr  Ile Ser  Ser Val Val  Ser Gln  Val Ser Ala
    1115                1120                1125

Ser Asn  Pro Gly Leu  Ser Gly  Cys Asp Val  Leu Val  Gln Ala Leu
    1130                1135                1140

Leu Glu  Val Val Ser  Ala Leu  Val Ser Ile  Leu Gly  Ser Ser Ser
    1145                1150                1155

Ile Gly  Gln Ile Asn  Tyr Gly  Ala Ser Ala  Gln Tyr  Thr Gln Met
    1160                1165                1170

Val Gly  Gln Ser Val  Ala Gln  Ala Leu Ala
    1175                1180

<210> SEQ ID NO 5
<211> LENGTH: 24
<212> TYPE: PRT
<213> ORGANISM: Artificial
<220> FEATURE:
<223> OTHER INFORMATION: His tag and start codon

<400> SEQUENCE: 5

Met His His His His  His His  His His His  Ser Ser  Gly Ser Ser
1                5                   10                  15

Leu Glu Val Leu Phe  Gln Gly  Pro
                20

<210> SEQ ID NO 6
<211> LENGTH: 660
<212> TYPE: PRT
<213> ORGANISM: Artificial
<220> FEATURE:
<223> OTHER INFORMATION: recombinant spider silk protein ADF3Kai

<400> SEQUENCE: 6

Met His His His His  His His  His His His  Ser Ser  Gly Ser Ser
1                5                   10                  15

Leu Glu Val Leu Phe  Gln Gly  Pro Ala Arg  Ala Gly  Ser Gln Gln
                20                  25                  30

Gly Pro Gly Gln Gln  Gly Pro  Gly Gln Gln  Gly Pro  Gly Gln Gln
            35                  40                  45

Pro Tyr Gly Pro Gly  Ala Ser  Ala Ala Ala  Ala Ala  Gly Gly Tyr
        50                  55                  60

Gly Pro Gly Ser Gly  Gln Gln  Gly Pro Gln  Gln Gly  Pro Gly Gln
65                  70                  75                  80

Gln Gly Pro Gly Gly  Gln Gly  Pro Tyr Gly  Pro Gly  Ala Ser Ala
            85                  90                  95

Ala Ala Ala Ala Gly  Gly Tyr  Gly Pro Gly  Ser Gly  Gln Gln Gly Pro
                100                 105                 110

Gly Gly Gln Gly Pro  Tyr Gly  Pro Gly Ser  Ser Ala  Ala Ala Ala
            115                 120                 125
```

```
Ala Gly Gly Asn Gly Pro Gly Ser Gly Gln Gln Gly Ala Gly Gln Gln
130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
            165                 170                 175

Pro Gly Gly Gln Gly Pro Tyr Gly Pro Gly Ala Ser Ala Ala Ala Ala
                180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala
210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gln Gln Gly Pro Tyr Gly
                245                 250                 255

Pro Gly Ala Ser Ala Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
        275                 280                 285

Tyr Gly Pro Gly Ala Ser Ala Ala Ser Ala Ala Ser Gly Gly Tyr Gly
        290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Ala Gly Gly
                325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gln Gln Gly Pro Tyr Gly
                355                 360                 365

Pro Gly Ala Ser Ala Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
                405                 410                 415

Gln Gln Gly Pro Gly Gln Gln Gly Pro Gly Gln Gln Gly Pro Gly Gly
                420                 425                 430

Gln Gly Ala Tyr Gly Pro Gly Ala Ser Ala Ala Gly Ala Ala Gly Gly
            435                 440                 445

Gly Tyr Gly Pro Gly Ser Gly Gln Gln Gly Pro Gly Gln Gln Gly Pro
        450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
                485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
            515                 520                 525

Gly Gly Gln Gly Pro Tyr Gly Pro Gly Ala Ala Ser Ala Ala Val Ser
530                 535                 540

Val Gly Gly Tyr Gly Pro Gln Ser Ser Ser Val Pro Val Ala Ser Ala
```

```
          545                 550                 555                 560
Val Ala Ser Arg Leu Ser Ser Pro Ala Ala Ser Ser Arg Val Ser Ser
                    565                 570                 575
Ala Val Ser Ser Leu Val Ser Ser Gly Pro Thr Lys His Ala Ala Leu
                580                 585                 590
Ser Asn Thr Ile Ser Ser Val Val Ser Gln Val Ser Ala Ser Asn Pro
            595                 600                 605
Gly Leu Ser Gly Cys Asp Val Leu Val Gln Ala Leu Leu Glu Val Val
        610                 615                 620
Ser Ala Leu Val Ser Ile Leu Gly Ser Ser Ser Ile Gly Gln Ile Asn
625                 630                 635                 640
Tyr Gly Ala Ser Ala Gln Tyr Thr Gln Met Val Gly Gln Ser Val Ala
                    645                 650                 655
Gln Ala Leu Ala
        660

<210> SEQ ID NO 7
<211> LENGTH: 1983
<212> TYPE: DNA
<213> ORGANISM: Artificial
<220> FEATURE:
<223> OTHER INFORMATION: recombinant DNA of spider silk protein gene
      ADF3Kai

<400> SEQUENCE: 7
atgcatcacc atcatcatca tcaccaccac cattcctcgg gctcatcctt ggaagtgtta      60
tttcaaggac cagcacgagc cggttcggga caacaagggc ctggccagca gggcccaggt     120
caacaagggc caggacagca gggtccttat gggcccggcg caagcgcagc agctgcggcc     180
gctggtggct atggtcctgg ctccggtcaa cagggcccct cgcaacaagg tcccgggcag     240
caaggtcctg gtggccaggg tccctacggg ccggggcga gtgcggcagc agccgctgca     300
ggcggttatg gtccaggaag cggacagcaa ggtccgggag gtcaaggtcc gtatggccca     360
ggctctagcg cggctgccgc tgccgcgggt ggcaacggac agggagcgg acaacagggc     420 gcgggacaac agggtccagg acagcaaggc caggggcgt cggcggctgc agcggcggcc     480
ggaggctatg acccggctc aggacaacag ggaccgggtc aacaaggacc cggtggccaa     540
ggcccctatg gccgggcgc cagcgcggcc gcagccgccg cgggcgggta cggcccggt      600 agcggccagg accaggtca gcaggggcca ggaggtcagg gcccatacgg tccgggcgca     660
tccgcggcgg cggcagcggc aggtggctac ggtcccggaa gcggccaaca ggggccaggg     720
caacaaggac caggacaaca aggtcctggg ggccaaggac cgtatggacc aggagcatca     780
gctgcagccg cggcagctgg cggttacggt ccaggctacg ccagcagggg tccgggtcag     840
cagggaccgg gaggccaggg gccttatggc cctggcgctt ccgcagccag tgccgcttct     900
ggaggatacg ggccgggaag cggtcagcaa ggccctggcc aacaaggacc tggaggccaa     960
gggccctacg gccaggagc ctcggcagcc gcagctgccg caggtgggta tgggccaggt    1020
agcgggcaac aagggccggg tcagcaagga ccggggcaac agggacctgg gcagcaagga    1080
cccgggggtc aaggcccgta cggacctggt gcgtctgcag ctgctgctgc ggctggtgga    1140
tatggtccgg gatcggggca gcagggtccc ggtcagcagg ccctggtca gcaagggcca    1200 ggccaacagg gacccggaca acaaggcccg gtcaacagg gtcctggaca gcagggccg     1260 ggccaacaag gcctgggca acaggtccg ggggacagg gggcctatgg gcctggcgca    1320
tctgccgccg ctggcgcagc cggtgggtac gggcctgggt caggtcaaca ggggcctggt    1380
```

```
caacaaggcc ccgggcaaca gggccccggc cagcaaggtc cagggcagca gggcccggga    1440 cagcaaggc ctggacaaca ggggcccgga cagcaggga cttacgggcc cggtgcgagc    1500
gcagcggccg ccgccgcagg gggatatggc cccggatcgg gccagcaggg accaggccag    1560
caaggacctg gccaacaggg cccgggggt caggggccgt atggtccgg cgctgcaagt    1620 gctgcagtgt ccgttggagg ttacggccct cagtcttcgt ctgttccggt ggcgtccgca    1680
gttgcgagta gactgtcttc acctgctgct tcatcgcgag tatcgagcgc tgtttcgtct    1740
cttgtctcgt cgggtcccac gaaacatgcc gcccttcaa atacgatttc atctgtagtg    1800
tcccaagtta gtgcaagtaa cccggggtta tccggatgcg acgttctcgt tcaggcactc    1860
ctagaagtag tatccgcgtt ggtgagcatc ttaggcagct cctcgatagg tcaaataaac    1920
tatggtgctt cagcccagta tacacagatg gtgggacaga gcgtcgcgca ggcattggct    1980
taa                                                                  1983
```

```
<210> SEQ ID NO 8
<211> LENGTH: 1154
<212> TYPE: PRT
<213> ORGANISM: Artificial
<220> FEATURE:
<223> OTHER INFORMATION: recombinant spider silk protein
      ADF3Kai-Large-NRSH1

<400> SEQUENCE: 8

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gly Pro Gly Gln
65                  70                  75                  80

Gln Gly Pro Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala
        115                 120                 125

Ala Gly Gly Asn Gly Pro Gly Ser Gly Gln Gln Gly Ala Gly Gln Gln
    130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala
            180                 185                 190

Ala Ala Gly Gly Tyr Gly Pro Gly Ser Gly Gln Gly Pro Gly Gln Gln
        195                 200                 205

Gly Pro Gly Gly Gln Gly Pro Tyr Gly Pro Gly Ala Ser Ala Ala Ala
    210                 215                 220

Ala Ala Ala Gly Gly Tyr Gly Pro Gly Ser Gly Gln Gln Gly Pro Gly
225                 230                 235                 240
```

```
Gln Gln Gly Pro Gly Gln Gln Gly Pro Gly Gln Gly Pro Tyr Gly
            245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gln Gly Pro
            275                 280                 285

Tyr Gly Pro Gly Ala Ser Ala Ala Ser Ala Ala Ser Gly Gly Tyr
            290                 295                 300

Pro Gly Ser Gly Gln Gln Gly Pro Gly Gln Gln Gly Pro Gly Gln
305                 310                 315                 320

Gly Pro Tyr Gly Pro Gly Ala Ser Ala Ala Ala Ala Ala Gly Gly
            325                 330                 335

Tyr Gly Pro Gly Ser Gly Gln Gln Gly Pro Gly Gln Gln Gly Pro
            340                 345                 350

Gly Gln Gly Pro Gly Gln Gln Gly Pro Gly Gln Gln Gly Pro Tyr Gly
            355                 360                 365

Pro Gly Ala Ser Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro
385                 390                 395                 400

Gly Gln Gln Gly Pro Gly Gln Gln Gly Pro Gly Gln Gln Gly Pro Gly
            405                 410                 415

Gln Gln Gly Pro Gly Gln Gln Gly Pro Gly Gln Gln Gly Pro Gly Gly
            420                 425                 430

Gln Gly Ala Tyr Gly Pro Gly Ala Ser Ala Ala Gly Ala Ala Gly
            435                 440                 445

Gly Tyr Gly Pro Gly Ser Gly Gln Gln Gly Pro Gly Gln Gln Gly Pro
            450                 455                 460

Gly Gln Gln Gly Pro Gly Gln Gln Gly Pro Gly Gln Gln Gly Pro Gly
465                 470                 475                 480

Gln Gln Gly Pro Gly Gln Gln Gly Pro Gly Gln Gln Gly Pro Tyr Gly
            485                 490                 495

Pro Gly Ala Ser Ala Ala Ala Ala Ala Gly Gly Tyr Gly Pro Gly
            500                 505                 510

Ser Gly Gln Gln Gly Pro Gly Gln Gln Gly Pro Gly Gln Gln Gly Pro
            515                 520                 525

Gly Gly Gln Gly Pro Tyr Gly Pro Gly Ala Ala Ser Ala Ala Val Ser
            530                 535                 540

Val Ser Arg Ala Arg Ala Gly Ser Gly Gln Gln Gly Pro Gly Gln Gln
545                 550                 555                 560

Gly Pro Gly Gln Gln Gly Pro Gly Gln Gln Gly Pro Tyr Gly Pro Gly
            565                 570                 575

Ala Ser Ala Ala Ala Ala Ala Ala Gly Gly Tyr Gly Pro Gly Ser Gly
            580                 585                 590

Gln Gln Gly Pro Ser Gln Gly Pro Gly Gln Gln Gly Pro Gly Gly
            595                 600                 605

Gln Gly Pro Tyr Gly Pro Gly Ala Ser Ala Ala Ala Ala Ala Gly
            610                 615                 620

Gly Tyr Gly Pro Gly Ser Gly Gln Gln Gly Pro Gly Gln Gln Gly Pro
625                 630                 635                 640

Tyr Gly Pro Gly Ser Ser Ala Ala Ala Ala Ala Ala Gly Gly Asn Gly
            645                 650                 655

Pro Gly Ser Gly Gln Gln Gly Ala Gly Gln Gln Gly Pro Gly Gln Gln
```

```
              660                 665                 670
Gly Pro Gly Ala Ser Ala Ala Ala Ala Ala Gly Gly Tyr Gly Pro
            675                 680                 685
Gly Ser Gly Gln Gln Gly Pro Gly Gln Gln Gly Pro Gly Gly Gln
690                 695                 700
Pro Tyr Gly Pro Gly Ala Ser Ala Ala Ala Ala Ala Gly Gly Tyr
705                 710                 715                 720
Gly Pro Gly Ser Gly Gln Gly Pro Gly Gln Gln Gly Pro Gly Gln
                725                 730                 735
Gly Pro Tyr Gly Pro Gly Ala Ser Ala Ala Ala Ala Ala Gly Gly
                740                 745                 750
Tyr Gly Pro Gly Ser Gly Gln Gln Gly Pro Gly Gln Gln Gly Pro Gly
            755                 760                 765
Gln Gln Gly Pro Gly Gly Gln Gly Pro Tyr Gly Pro Gly Ala Ser Ala
            770                 775                 780
Ala Ala Ala Ala Gly Gly Tyr Gly Pro Gly Tyr Gly Gln Gln Gly
785                 790                 795                 800
Pro Gly Gln Gln Gly Pro Gly Gly Gln Gly Pro Tyr Gly Pro Gly Ala
                805                 810                 815
Ser Ala Ala Ser Ala Ala Ser Gly Gly Tyr Gly Pro Gly Ser Gly Gln
                820                 825                 830
Gln Gly Pro Gly Gln Gln Gly Pro Gly Gly Gln Gly Pro Tyr Gly Pro
            835                 840                 845
Gly Ala Ser Ala Ala Ala Ala Ala Gly Gly Tyr Gly Pro Gly Ser
850                 855                 860
Gly Gln Gln Gly Pro Gly Gln Gln Gly Pro Gly Gln Gln Gly Pro Gly
865                 870                 875                 880
Gln Gln Gly Pro Gly Gly Gln Gly Pro Tyr Gly Pro Gly Ala Ser Ala
                885                 890                 895
Ala Ala Ala Ala Gly Gly Tyr Gly Pro Gly Ser Gly Gln Gln Gly
                900                 905                 910
Pro Gly Gln Gln Gly Pro Gly Gln Gln Gly Pro Gly Gln Gln Gly Pro
            915                 920                 925
Gly Gln Gln Gly Pro Gly Gln Gln Gly Pro Gly Gln Gln Gly Pro Gly
930                 935                 940
Gln Gln Gly Pro Gly Gln Gln Gly Pro Gly Gln Gly Ala Tyr Gly
945                 950                 955                 960
Pro Gly Ala Ser Ala Ala Ala Gly Ala Ala Gly Gly Tyr Gly Pro Gly
                965                 970                 975
Ser Gly Gln Gln Gly Pro Gly Gln Gln Gly Pro Gly Gln Gln Gly Pro
                980                 985                 990
Gly Gln Gln Gly Pro Gly Gln Gln  Gly Pro Gly Gln Gln  Gly Pro Gly
                995                 1000                1005
Gln Gln  Gly Pro Gly Gln  Gly Pro Tyr Gly Pro  Gly Ala Ser
            1010                1015                1020
Ala Ala  Ala Ala Ala Ala Gly  Gly Tyr Gly Pro Gly  Ser Gly Gln
            1025                1030                1035
Gln Gly  Pro Gly Gln Gln Gly  Pro Gly Gln Gln Gly  Pro Gly Gly
            1040                1045                1050
Gln Gly  Pro Tyr Gly Pro Gly  Ala Ala Ser Ala Ala  Val Ser Val
            1055                1060                1065
Gly Gly  Tyr Gly Pro Gln Ser  Ser Ser Val Pro Val  Ala Ser Ala
            1070                1075                1080
```

| Val | Ala | Ser | Arg | Leu | Ser | Ser | Pro | Ala | Ala | Ser | Ser | Arg | Val | Ser |
|-----|-----|-----|-----|-----|-----|-----|-----|-----|-----|-----|-----|-----|-----|-----|
| 1085 | | | | 1090 | | | | | 1095 | | | | | |

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu
    1145                1150

<210> SEQ ID NO 9
<211> LENGTH: 3552
<212> TYPE: DNA
<213> ORGANISM: Artificial
<220> FEATURE:
<223> OTHER INFORMATION: recombinant DNA of spider silk protein gene
      ADF3Kai-Large

<400> SEQUENCE: 9

```
atgcatcacc atcatcatca tcaccaccac cattcctcgg gctcatcctt ggaagtgtta      60
tttcaaggac cagcacgagc cggttcggga caacaagggc ctggccagca gggcccaggt     120
caacaagggc caggacagca gggtccttat gggcccggcg caagcgcagc agctgcggcc     180
gctggtggct atggtcctgg ctccggtcaa cagggccctt cgcaacaagg tcccgggcag     240
caaggtcctg gtggccaggg tccctacggg ccggggcga gtgcggcagc agccgctgca      300
ggcggttatg gtccaggaag cggacagcaa ggtccgggag gtcaaggtcc gtatggccca     360
ggctctagcg cggctgccgc tgccgcgggt ggcaacggac agggagcgg acaacagggc      420 gcgggacaac agggtccagg acagcaaggc ccaggggcgt cggcggctgc agcggcggcc     480
ggaggctatg acccggctc aggacaacag ggaccgggtc aacaaggacc cggtggccaa      540 ggccccatg gcccggcgc cagcgcggcc gcagccgccg cgggcgggta cggccccggt       600
agcggccagg gaccaggtca gcaggggcca ggaggtcagg gcccatacgg tccgggcgca     660
tccgcggcgg cggcagcggc aggtggctac ggtccccggaa cgggcaaca ggggccaggg     720 caacaaggac caggacaaca aggtcctggg ggccaaggac cgtatggacc aggagcatca     780
gctgcagccg cggcagctgg cggttacggt ccaggctacg gccagcaggg tccgggtcag     840
cagggaccgg gaggccaggg gccttatggc cctggcgctt ccgcagccag tgccgcttct     900
ggaggatacg gccgggaag cggtcagcaa ggccctggcc aacaaggacc tggaggccaa     960
gggccctacg gcccaggagc ctcggcagcc gcagctgccg caggtgggta tgggccaggt    1020
agcgggcaac aagggccggg tcagcaagga ccggggcaac agggacctgg cagcaagga    1080 cccgggggtc aaggcccgta cggacctggt gcgtctgcag ctgctgctgc ggctggtgga    1140
tatggtccgg gatcgggcga gcagggtccc ggtcagcagg gcctggtca gcaagggcca    1200 ggccaacagg gaccggaca caaggcccg gtcaacagg gtcctggaca gcaggggccg      1260
ggccaacaag gccctgggca acaggtccg ggggacagg gggcctatgg gcctggcgca     1320
tctgccgccg ctggcgcagc cggtgggtac gggcctggt caggtcaaca ggggcctgt      1380 caacaaggcc ccgggcaaca gggcccggc agcaaggtc agggcagca gggcccggga      1440 cagcaagggc ctgacaaca ggggcccgga cagcaggga cttacgggcc cggtgcgagc      1500
gcagcggccg ccgccgcagg gggatatggc cccggatcgg gccagcaggg accaggccag    1560
```

| | |
|---|---|
| caaggacctg gccaacaggg cccgggggt caggggccgt atggtcccgg cgctgcaagt | 1620 |
| gctgcagtgt ccgtttctag agcacgagcc ggttcgggac aacaagggcc tggccagcag | 1680 |
| ggcccaggtc aacaagggcc aggacagcag ggtccttatg ggcccggcgc aagcgcagca | 1740 |
| gctgcggccg ctggtggcta tggtcctggc tccggtcaac agggcccttc gcaacaaggt | 1800 |
| cccgggcagc aaggtcctgg tggccagggt ccctacgggc cgggggcgag tgcggcagca | 1860 |
| gccgctgcag gcggttatgg tccaggaagc ggacagcaag gtccgggagg tcaaggtccg | 1920 |
| tatggcccag gctctagcgc ggctgccgct gccgcgggtg caacggacc agggagcgga | 1980 |
| caacagggcg cgggacaaca gggtccagga cagcaaggcc caggggcgtc ggcggctgca | 2040 |
| gcggcggccg gaggctatgg acccggctca ggacaacagg gaccgggtca acaaggaccc | 2100 |
| ggtggccaag gccccatgg cccgggcgcc agcgcggccg cagccgccgc gggcgggtac | 2160 |
| ggccccggta gcgccagggg accaggtcag cagggggccag gaggtcaggg cccatacggt | 2220 |
| ccgggcgcat ccgcggcggc ggcagcggca ggtggctacg gtcccggaag cggccaacag | 2280 |
| gggccagggc aacaaggacc aggacaacaa ggtcctgggg gccaaggacc gtatggacca | 2340 |
| ggagcatcag ctgcagccgc ggcagctggc ggttacggtc caggctacgg ccagcagggt | 2400 |
| ccgggtcagg agggaccggg aggccagggg cctttatggcc ctggcgcttc cgcagccagt | 2460 |
| gccgcttctg gaggatacgg gccgggaagc ggtcagcaag gcctggcca caaggacct | 2520 |
| ggaggccaag ggccctacgg cccaggagcc tcggcagccg cagctgccgc aggtgggtat | 2580 |
| gggccaggta gcgggcaaca agggccgggt cagcaaggac cggggcaaca gggacctggg | 2640 |
| cagcaaggac ccggggggtca aggcccgtac ggacctggtg cgtctgcagc tgctgctgcg | 2700 |
| gctggtggat atggtccggg atcggggcag cagggtcccg gtcagcaggg ccctggtcag | 2760 |
| caagggccag ccaacaggg acccggacaa caaggcccgg gtcaacaggg tcctggacag | 2820 |
| caggggccgg ccaacaagg ccctgggcaa caggtccgg ggggacaggg ggcctatggg | 2880 |
| cctggcgcat ctgccgccgc tggcgcagcc ggtgggtacg ggcctgggtc aggtcaacag | 2940 |
| gggcctggtc aacaaggccc cggcaacag ggccccggcc agcaaggtcc agggcagcag | 3000 |
| ggcccgggac agcaagggcc tggacaacag gggcccggac agcagggacc ttacgggccc | 3060 |
| ggtgcgagcg cagcggccgc cgccgcaggg ggatatggcc ccggatcggg ccagcaggga | 3120 |
| ccaggccagc aaggacctgg ccaacagggc ccggggggtc aggggccgta tggtcccggc | 3180 |
| gctgcaagtg ctgcagtgtc cgttggaggt tacggccctc agtcttcgtc tgttccggtg | 3240 |
| gcgtccgcag ttgcgagtag actgtcttca cctgctgctt catcgcgagt atcgagcgct | 3300 |
| gtttcgtctc ttgtctcgtc gggtcccacg aaacatgccg ccctttcaaa tacgatttca | 3360 |
| tctgtagtgt cccaagttag tgcaagtaac ccggggttat ccggatgcga cgttctcgtt | 3420 |
| caggcactcc tagaagtagt atccgcgttg gtgagcatct taggcagctc ctcgataggt | 3480 |
| caaataaact atggtgcttc agcccagtat acacagatgg tgggacagag cgtcgcgcag | 3540 |
| gcattggctt aa | 3552 |

<210> SEQ ID NO 10
<211> LENGTH: 3465
<212> TYPE: DNA
<213> ORGANISM: Artificial
<220> FEATURE:
<223> OTHER INFORMATION: recombinant DNA of spider silk protein gene
     ADF3Kai-Large-NRSH1

<400> SEQUENCE: 10

-continued

```
atgcatcacc atcatcatca tcaccaccac cattcctcgg gctcatcctt ggaagtgtta      60
tttcaaggac cagcacgagc cggttcggga caacaagggc ctggccagca gggcccaggt     120
caacaagggc caggacagca gggtccttat gggcccggcg caagcgcagc agctgcggcc     180
gctggtggct atggtcctgg ctccggtcaa cagggccctt cgcaacaagg tcccgggcag     240
caaggtcctg gtggccaggg tccctacggg ccggggcga gtgcggcagc agccgctgca     300
ggcggttatg gtccaggaag cggacagcaa ggtccgggag tcaaggtcc gtatggccca     360 ggctctagcg cggctgccgc tgccgcgggt ggcaacggac cagggagcgg acaacagggc     420
gcgggacaac agggtccagg acagcaaggc ccaggggcgt cggcggctgc agcggcggcc     480
ggaggctatg acccggctc aggacaacag ggaccgggtc aacaaggacc cggtggccaa     540
ggcccctatg cccgggcgc cagcgcggcc gcagccgccg cgggcgggta cggcccggt     600 agcggccagg gaccaggtca gcaggggcca ggaggtcagg gcccatacgg tccgggcgca     660
tccgcggcgg cggcagcggc aggtggctac ggtcccggaa gcggccaaca ggggccaggg     720
caacaaggac caggacaaca aggtcctggg ggccaaggac cgtatggacc aggagcatca     780
gctgcagccg cggcagctgg cggttacggt ccaggctacg gccagcaggg tccgggtcag     840
cagggaccgg gaggccaggg gccttatggc cctggcgctt ccgcagccag tgccgcttct     900
ggaggatacg ggccgggaag cggtcagcaa ggccctggcc aacaaggacc tggaggccaa     960
gggccctacg gcccaggagc ctcggcagcc gcagctgccg caggtgggta tgggccaggt    1020
agcgggcaac aagggccggg tcagcaagga ccggggcaac agggacctgg gcagcaagga    1080
cccgggggtc aaggcccgta cggacctggt gcgtctgcag ctgctgctgc ggctggtgga    1140
tatggtccgg gatcggggca gcagggtccc ggtcagcagg gccctggtca gcaagggcca    1200
ggccaacagg gacccggaca acaaggcccg ggtcaacagg gtcctggaca gcaggggccg    1260
ggccaacaag gccctgggca cagggtccg ggggacagg gggcctatgg gcctggcgca    1320
tctgccgccg ctggcgcagc cggtgggtac gggcctgggt caggtcaaca ggggcctggt    1380
caacaaggcc ccgggcaaca gggccccggc cagcaaggtc cagggcagca gggcccggga    1440
cagcaagggc ctgacaaca ggggcccgga cagcaggga cttacgggcc cggtgcgagc    1500
gcagcggccg ccgccgcagg gggatatggc cccggatcgg ccagcagggg accaggccag    1560
caaggacctg gccaacaggg cccgggggt caggggccgt atggtcccgg cgctgcaagt    1620
gctgcagtgt ccgtttctag agcacgagcc ggttcgggac aacaagggcc tggccagcag    1680
ggcccaggtc aacaagggcc aggacagcag ggtccttatg ggcccggcgc aagcgcagca    1740
gctgcggccg ctggtggcta tggtcctggc tccggtcaac agggcccttc gcaacaaggt    1800
cccgggcagc aaggtcctgg tggccagggt ccctacgggc cggggcgag tgcggcagca    1860 gccgctgcag gcggttatgg tccaggaagc ggacagcaag gtccgggagg tcaaggtccg    1920
tatggcccag gctctagcgc ggctgccgct gccgcgggtg gcaacggacc agggagcgga    1980
caacagggcg cggacaaca gggtccagga cagcaaggcc aggggcgtc ggcggctgca    2040 gcggcggccg gaggctatgg acccggctca ggacaacagg gaccgggtca acaaggaccc    2100 ggtgccaag gcccctatgg cccgggcgcc agcgcggccg cagccgccgc gggcgggtac    2160
ggccccggta gcggccaggg accaggtcag caggggccag gaggtcaggg cccatacggt    2220
ccgggcgcat ccgcggcggc ggcagcggca ggtggctacg gtcccggaag cggccaacag    2280
gggccagggc aacaaggacc aggacaacaa ggtcctgggg gccaaggacc gtatggacca    2340
ggagcatcag ctgcagccgc ggcagctggc ggttacggtc caggctacgg ccagcagggt    2400
```

-continued

```
ccgggtcagc agggaccggg aggccagggg ccttatggcc ctggcgcttc cgcagccagt    2460
gccgcttctg gaggatacgg gccgggaagc ggtcagcaag gccctggcca acaaggacct    2520
ggaggccaag ggccctacgg cccaggagcc tcggcagccg cagctgccgc aggtgggtat    2580
gggccaggta gcgggcaaca agggccgggt cagcaaggac cggggcaaca gggacctggg    2640
cagcaaggac ccgggggtca aggcccgtac ggacctggtg cgtctgcagc tgctgctgcg    2700
gctggtggat atggtccggg atcggggcag cagggtcccg gtcagcaggg ccctggtcag    2760
caagggccag gccaacaggg acccggacaa caaggcccgg gtcaacaggg tcctggacag    2820
caggggccgg gccaacaagg ccctgggcaa cagggtccgg ggggacaggg ggcctatggg    2880
cctggcgcat ctgccgccgc tggcgcagcc ggtgggtacg ggcctgggtc aggtcaacag    2940
gggcctggtc aacaaggccc cgggcaacag ggccccggcc agcaaggtcc agggcagcag    3000
ggcccgggac agcaagggcc tggacaacag gggcccggac agcagggacc ttacgggccc    3060
ggtgcgagcg cagcggccgc cgccgcaggg ggatatggcc ccggatcggg ccagcaggga    3120
ccaggccagc aaggacctgg ccaacagggc ccgggggtc aggggccgta tggtcccggc    3180
gctgcaagtg ctgcagtgtc cgttggaggt tacggccctc agtcttcgtc tgttccggtg    3240
gcgtccgcag ttgcgagtag actgtcttca cctgctgctt catcgcgagt atcgagcgct    3300
gtttcgtctc ttgtctcgtc gggtcccacg aaacatgccg cccttccaaa tacgatttca    3360
tctgtagtgt cccaagttag tgcaagtaac ccggggttat ccggatgcga cgttctcgtt    3420
caggcactcc tagaagtagt atccgcgttg gtgagcatct tataa                   3465
```

<210> SEQ ID NO 11
<211> LENGTH: 20
<212> TYPE: DNA
<213> ORGANISM: Artificial
<220> FEATURE:
<223> OTHER INFORMATION: T7 promoter primer

<400> SEQUENCE: 11
taatacgact cactataggg                                                20

<210> SEQ ID NO 12
<211> LENGTH: 27
<212> TYPE: DNA
<213> ORGANISM: Artificial
<220> FEATURE:
<223> OTHER INFORMATION: Rep Xba I primer

<400> SEQUENCE: 12
tctagaaacg gacactgcag cacttgc                                        27

<210> SEQ ID NO 13
<211> LENGTH: 19
<212> TYPE: DNA
<213> ORGANISM: Artificial
<220> FEATURE:
<223> OTHER INFORMATION: T7 terminator primer

<400> SEQUENCE: 13
gctagttatt gctcagcgg                                                 19

<210> SEQ ID NO 14
<211> LENGTH: 28
<212> TYPE: DNA
<213> ORGANISM: Artificial
<220> FEATURE:

<223> OTHER INFORMATION: Xba I Rep primer

<400> SEQUENCE: 14
tctagagcac gagccggttc gggacaac                                              28

<210> SEQ ID NO 15
<211> LENGTH: 434
<212> TYPE: PRT
<213> ORGANISM: Artificial
<220> FEATURE:
<223> OTHER INFORMATION: Recombinang spider silk protein ADF4Kai

<400> SEQUENCE: 15

Met His His His His His His His His His Ser Ser Gly Ser Ser
1               5                   10                  15

Leu Glu Val Leu Phe Gln Gly Pro Ala Gly Ser Ser Ala Ala Ala
            20                  25                  30

Ala Ala Ala Ser Gly Ser Gly Gly Tyr Gly Pro Glu Asn Gln Gly Pro
            35                  40                  45

Ser Gly Pro Val Ala Tyr Gly Pro Gly Gly Pro Val Ser Ser Ala Ala
        50                  55                  60

Ala Ala Ala Ala Ala Gly Ser Gly Pro Gly Gly Tyr Gly Pro Glu Asn
65                  70                  75                  80

Gln Gly Pro Ser Gly Pro Gly Gly Tyr Gly Pro Gly Gly Ser Gly Ser
                85                  90                  95

Ser Ala Ala Ala Ala Ala Ala Ala Ser Gly Pro Gly Gly Tyr Gly
            100                 105                 110

Pro Gly Ser Gln Gly Pro Ser Gly Pro Gly Gly Ser Gly Tyr Gly
            115                 120                 125

Pro Gly Ser Gln Gly Ala Ser Gly Pro Gly Pro Gly Ala Ser Ala
            130                 135                 140

Ala Ala Ala Ala Ala Ala Ala Ser Gly Pro Gly Gly Tyr Gly
145                 150                 155                 160

Pro Gly Ser Gln Gly Pro Ser Gly Pro Gly Ala Tyr Gly Pro Gly Gly
                165                 170                 175

Pro Gly Ser Ser Ala Ala Ala Ala Ala Ala Ser Gly Pro Gly
            180                 185                 190

Gly Tyr Gly Pro Gly Ser Gln Gly Pro Ser Gly Pro Gly Val Tyr Gly
                195                 200                 205

Pro Gly Gly Pro Gly Ser Ser Ala Ala Ala Ala Ala Ala Gly Ser
            210                 215                 220

Gly Pro Gly Gly Tyr Gly Pro Glu Asn Gln Gly Pro Ser Gly Pro Gly
225                 230                 235                 240

Gly Tyr Gly Pro Gly Gly Ser Gly Ser Ser Ala Ala Ala Ala Ala
                245                 250                 255

Ala Ala Ser Gly Pro Gly Gly Tyr Gly Pro Gly Ser Gln Gly Pro Ser
            260                 265                 270

Gly Pro Gly Gly Ser Gly Tyr Gly Pro Gly Ser Gln Gly Gly Ser
            275                 280                 285

Gly Pro Gly Ala Ser Ala Ala Ala Ala Ala Ala Ala Ser Gly Pro
            290                 295                 300

Gly Gly Tyr Gly Pro Gly Ser Gln Gly Pro Ser Gly Pro Gly Tyr Gln
305                 310                 315                 320

Gly Pro Ser Gly Pro Gly Ala Tyr Gly Pro Ser Pro Ser Ala Ser Ala
                325                 330                 335

```
Ser Val Ala Ala Ser Val Tyr Leu Arg Leu Gln Pro Arg Leu Glu Val
            340                 345                 350

Ser Ser Ala Val Ser Ser Leu Val Ser Gly Pro Thr Asn Gly Ala
        355                 360                 365

Ala Val Ser Gly Ala Leu Asn Ser Leu Val Ser Gln Ile Ser Ala Ser
    370                 375                 380

Asn Pro Gly Leu Ser Gly Cys Asp Ala Leu Val Gln Ala Leu Leu Glu
385                 390                 395                 400

Leu Val Ser Ala Leu Val Ala Ile Leu Ser Ala Ser Ile Gly Gln
                405                 410                 415

Val Asn Val Ser Ser Val Ser Gln Ser Thr Gln Met Ile Ser Gln Ala
            420                 425                 430

Leu Ser

<210> SEQ ID NO 16
<211> LENGTH: 1305
<212> TYPE: DNA
<213> ORGANISM: Artificial
<220> FEATURE:
<223> OTHER INFORMATION: Recombinant DNA of spider silk protein gene
      ADF4Kai

<400> SEQUENCE: 16
atgcaccatc atcatcacca tcaccaccat catagcagtg gatcttcctt ggaagtatta      60
ttccagggtc ctgcgggttc aagcgcagct gctgcggctg ctgctagtgg cagcggggggt    120 tatggtcccg aaaatcaggg gccgtctgga cctgtggcat acggaccggg tggtccagtg     180
tccagtgccg cagctgccgc cgcagcaggc tcaggaccgg gaggctatgg ccagaaaaat     240
caagggccga gcgggccagg gggatatggt cctgggggta gcggatcaag cgcggctgca     300
gctgccgcgg ctgctagcgg tccgggcggg tacgccccgg gctctcaggg tccgagcggc     360
cctggcggga gtggtggtta tggccccggt tcccaaggtg catctggtcc aggtggtccg     420
ggtgctagcg cagcggccgc ggcggctgcc gcggccgcaa gtggccctgg aggatatggc     480
cctggttccc agggaccatc aggtcccggt gcgtatggac cgggcggccc cggaagcagc     540
gccgcagccg ctgccgcagc ggcttcagga ccaggaggtt acggcccagg cagtcaaggt     600
ccttcaggcc cgggtgttta cggtccaggc ggcccgggta gtagtgctgc agcggcggcc     660
gcagctggtt cgggacctgg tgggtatgga cctgaaaacc aaggcccatc ggggcctggt     720
ggctatggcc cgggcggtag tggatctagt gctgccgctg ccgctgctgc agccagcgga     780
cccgggggtt acgggcctgg tagccaggga ccgtctgggc caggtggcag tggagggtat     840
ggcccaggta gtcagggtgg ttccggccca ggtgcgagcg ctgcggcggc ggcagcagca     900
gcaagcggac ctggggcta tggtccaggg tcacagggcc cctcaggtcc aggatatcag      960
ggcccgtcag ggcctggggc ctatggacca agtccatctg ctagtgcctc tgtggcggcc    1020
tccgtgtatc ttcgcctcca acccgtttta gaggtaagtt ctgccgtttc ctctttggtg    1080
tcgagtggcc cgaccaacgg ggcagcagtg agcggcgcac tcaatagtct ggtttctcaa    1140
atatcagcat ctaacccggg tctgtctggt tgcgatgcgt tggttcaggc actgttagaa    1200
cttgtgtccg cgcttgtggc gattctttct agccgcgtcga ttggtcaagt gaatgtaagt    1260
agcgtgtctc agagcaccca tgatgatctca caggcgctgt cttaa                   1305

<210> SEQ ID NO 17
<211> LENGTH: 355
<212> TYPE: PRT
```

<213> ORGANISM: Artificial
<220> FEATURE:
<223> OTHER INFORMATION: Recombinant spider silk protein MaSp2_N

<400> SEQUENCE: 17

Met His His His His His Ser Ser Gly Ser Ser Leu Glu Val Leu
1               5                   10                  15

Phe Gln Gly Pro Ala Arg Ala Gly Pro Gly Gly Tyr Arg Pro Gly Gln
                20                  25                  30

Gln Gly Pro Ser Gly Pro Gly Ser Ala Ala Ala Ala Ala Ala Ala
                35                  40                  45

Ala Gly Pro Gly Gly Tyr Gly Pro Gly Gln Gln Gly Pro Gly Gly Tyr
50                          55                      60

Gly Pro Gly Gln Gln Gly Pro Ser Gly Ala Gly Ser Ala Ala Ala
65                      70                      75                      80

Ala Ala Ala Gly Pro Gly Gln Gln Gly Leu Gly Gly Tyr Gly Pro Gly
                85                      90                      95

Gln Gln Gly Pro Gly Gly Tyr Gly Pro Gly Gln Gln Gly Pro Gly Gly
                100                 105                 110

Tyr Gly Pro Gly Ser Ala Ser Ala Ala Ala Ala Ala Gly Pro Gly
115                     120                     125

Gln Gln Gly Pro Gly Gly Tyr Gly Pro Gly Gln Gln Gly Pro Ser Gly
                130                 135                 140

Pro Gly Ser Ala Ser Ala Ala Ala Ala Ala Gly Pro Gly Gly Tyr
145                     150                     155                     160

Gly Pro Gly Gln Gln Gly Pro Gly Gly Tyr Ala Pro Gly Gln Gln Gly
                165                 170                 175

Pro Ser Gly Pro Gly Ser Ala Ala Ala Ala Ala Ala Arg Ala
                180                 185                 190

Gly Pro Gly Gly Tyr Gly Pro Ala Gln Gln Gly Pro Ser Gly Pro Gly
                195                 200                 205

Ile Ala Ala Ser Ala Ala Ser Gly Pro Gly Gly Tyr Gly Pro Ala
                210                 215                 220

Gln Gln Gly Pro Ala Gly Tyr Gly Pro Gly Ser Ala Val Ala Ala Ser
225                     230                     235                     240

Ala Gly Ala Gly Ser Ala Gly Tyr Gly Pro Gly Ser Gln Ala Ser Ala
                245                 250                 255

Ala Ala Ser Arg Leu Ala Ser Pro Asp Ser Gly Ala Arg Val Ala Ser
                260                 265                 270

Ala Val Ser Asn Leu Val Ser Ser Gly Pro Thr Ser Ser Ala Ala Leu
                275                 280                 285

Ser Ser Val Ile Ser Asn Ala Val Ser Gln Ile Gly Ala Ser Asn Pro
290                     295                     300

Gly Leu Ser Gly Cys Asp Val Leu Ile Gln Ala Leu Leu Glu Ile Val
305                     310                     315                     320

Ser Ala Cys Val Thr Ile Leu Ser Ser Ser Ile Gly Gln Val Asn
                325                 330                 335

Tyr Gly Ala Ala Ser Gln Phe Ala Gln Val Val Gly Gln Ser Val Leu
                340                 345                 350

Ser Ala Phe
        355

<210> SEQ ID NO 18
<211> LENGTH: 1068
<212> TYPE: DNA

<213> ORGANISM: Artificial
<220> FEATURE:
<223> OTHER INFORMATION: Recombinant DNA of spider silk protein gene MaSp2_N

<400> SEQUENCE: 18

```
atgcatcacc atcatcatca ttcttcaggc tcctcgctcg aagttctctt tcaaggaccg    60
gcgagagcag gacctggcgg ctatcgtcct ggacaacaag gccccagtgg cccgggaagc   120
gctgcggcgg cggcagctgc agcggcaggt cccggaggct atggcccgg acaacaggga    180
ccgggtggtt atgggccggg acagcaaggc cctagcggtg caggtagcgc ggcggccgca   240
gcagcggcgg gtcccggtca cagggcttag ggggctacg acctggtca gcagggcccc    300
ggtgggtatg gaccaggcca caagggccc ggcggatacg gtccgggttc agctagcgcc    360
gcggcagcgc tgccggacc agggcagcag gggccgggg gtatggtcc tgggcaacaa    420
ggaccaagcg gccagggag cgcgagtgca gccgcggccg ctgcaggccc aggtggctac   480
gggcctggcc agcaaggtcc aggcggttac gcacccgggc aacagggtcc tagtgggcca   540
ggaagtgcgg ctgcggcagc agcagctgcg agggcgggcc caggggggtta cggcccagca   600
cagcagggtc cgagcggtcc tggtattgcc gcaagcgcag cttccgctgg ccctggaggg   660
tacggtccag ctcagcaagg gccggctgga tatggtccag ttctgccgt ggctgcctca    720
gctggtgcgg gatcagcggg ttatggaccc ggctcacagg caagtgctgc agcctcgcgt   780
cttgcatccc ctgattcagg tgcacgcgtt gccagtgccg tctcaaacct cgtgtcaagt   840
ggtcccactt cgtcggctgc tttgtctagt gttatttcaa atgccgttag ccagatcggt   900
gcctcgaacc caggcttatc tggttgtgat gtccttattc aagcactgtt agagattgtt   960
tctgcttgtg tcacgatctt atcctcatcg tctatcggtc aggtcaatta tggtgccgcg  1020
tcgcagttcg cccaagttgt gggtcaaagc gttttgtcgg cgttttaa                1068
```

<210> SEQ ID NO 19
<211> LENGTH: 559
<212> TYPE: PRT
<213> ORGANISM: Artificial
<220> FEATURE:
<223> OTHER INFORMATION: Recombinant spider silk protein Flag_92_short2

<400> SEQUENCE: 19

Met His His His His His His His His His Ser Ser Gly Ser Ser
1               5                   10                  15

Leu Glu Val Leu Phe Gln Gly Pro Gly Ala Gly Gly Ser Gly Pro Gly
            20                  25                  30

Gly Ala Gly Pro Gly Gly Val Gly Pro Gly Gly Ser Gly Pro Gly Gly
        35                  40                  45

Val Gly Pro Gly Gly Ser Gly Pro Gly Gly Val Gly Pro Gly Gly Ser
    50                  55                  60

Gly Pro Gly Gly Val Gly Pro Gly Gly Ala Gly Pro Tyr Gly Pro
65                  70                  75                  80

Gly Gly Ser Gly Pro Gly Gly Ala Gly Ala Gly Pro Gly Gly
            85                  90                  95

Ala Tyr Gly Pro Gly Gly Ser Tyr Gly Pro Gly Gly Ser Gly Gly Pro
            100                 105                 110

Gly Gly Ala Gly Gly Pro Tyr Gly Pro Gly Gly Glu Gly Pro Gly Gly
        115                 120                 125

Ala Gly Gly Pro Tyr Gly Pro Gly Gly Ala Gly Pro Tyr Gly Pro
        130                 135                 140

```
Gly Gly Ala Gly Gly Pro Tyr Gly Pro Gly Glu Gly Pro Tyr
145                 150                 155                 160
Gly Pro Gly Gly Ser Tyr Gly Pro Gly Gly Ala Gly Pro Tyr Gly
            165                 170                 175
Pro Gly Gly Pro Tyr Gly Pro Gly Gly Glu Gly Pro Gly Ala Gly
            180                 185                 190
Gly Pro Tyr Gly Pro Gly Gly Val Gly Pro Gly Gly Gly Pro Gly
            195                 200                 205
Gly Tyr Gly Pro Gly Gly Ala Gly Pro Gly Gly Tyr Gly Pro Gly Gly
        210                 215                 220
Ser Gly Pro Gly Gly Tyr Gly Pro Gly Gly Ser Gly Pro Gly Gly Tyr
225                 230                 235                 240
Gly Pro Gly Gly Ser Gly Pro Gly Gly Tyr Gly Pro Gly Gly Ser Gly
                245                 250                 255
Pro Gly Gly Tyr Gly Pro Gly Gly Ser Gly Pro Gly Gly Ser Gly Pro
                260                 265                 270
Gly Gly Tyr Gly Pro Gly Gly Ser Gly Pro Gly Gly Ser Gly Pro Gly
            275                 280                 285
Gly Tyr Gly Pro Gly Gly Ser Gly Pro Gly Gly Tyr Gly Pro Gly Gly
        290                 295                 300
Ser Gly Pro Gly Gly Ser Gly Pro Gly Gly Tyr Gly Pro Gly Gly Ser
305                 310                 315                 320
Gly Pro Gly Gly Ser Gly Pro Gly Gly Tyr Gly Pro Gly Gly Ser Gly
                325                 330                 335
Pro Gly Gly Phe Gly Pro Gly Gly Phe Gly Pro Gly Gly Ser Gly Pro
                340                 345                 350
Gly Gly Tyr Gly Pro Gly Gly Ser Gly Pro Gly Gly Ala Gly Pro Gly
            355                 360                 365
Gly Val Gly Pro Gly Gly Phe Gly Pro Gly Gly Ala Gly Pro Gly Gly
        370                 375                 380
Ala Gly Pro Gly Gly Ala Gly Pro Gly Gly Ala Gly Pro Gly Gly Ala
385                 390                 395                 400
Gly Pro Gly Gly Ala Gly Pro Gly Gly Ala Gly Pro Gly Gly Ala Gly
                405                 410                 415
Pro Gly Gly Ala Gly Gly Ala Gly Gly Ala Gly Ala Gly Gly Ser
                420                 425                 430
Gly Gly Ala Gly Gly Ser Gly Gly Thr Thr Ile Ile Glu Asp Leu Asp
            435                 440                 445
Ile Thr Ile Asp Gly Ala Asp Gly Pro Ile Thr Ile Ser Glu Glu Leu
    450                 455                 460
Thr Ile Ser Ala Tyr Tyr Pro Ser Ser Arg Val Pro Asp Met Val Asn
465                 470                 475                 480
Gly Ile Met Ser Ala Met Gln Gly Ser Gly Phe Asn Tyr Gln Met Phe
            485                 490                 495
Gly Asn Met Leu Ser Gln Tyr Ser Ser Gly Ser Gly Thr Cys Asn Pro
                500                 505                 510
Asn Asn Val Asn Val Leu Met Asp Ala Leu Leu Ala Ala Leu His Cys
                515                 520                 525
Leu Ser Asn His Gly Ser Ser Phe Ala Pro Ser Pro Thr Pro Ala
                530                 535                 540
Ala Met Ser Ala Tyr Ser Asn Ser Val Gly Arg Met Phe Ala Tyr
545                 550                 555
```

<210> SEQ ID NO 20
<211> LENGTH: 1680
<212> TYPE: DNA
<213> ORGANISM: Artificial
<220> FEATURE:
<223> OTHER INFORMATION: Recombinant DNA of spider silk protein gene Flag_92_short2

<400> SEQUENCE: 20

```
atgcatcacc atcatcatca tcaccaccac cattcctcgg gctcatcctt ggaagtgtta        60
tttcaaggac caggagctgg agggtccggt ccgggcggcg ctggtccggg aggagtgggt       120
ccgggtggtt ctggacccgg tggagtaggt ccgggcggtt ccgtccggg aggcgtcgga       180
cctggtggat caggacctgg agtgtaggt cctggtggcg cgggtggccc ttacggccct       240
ggggggctctg gcccaggagg cgctggtggg gcaggagggc tggtggggc gtatggtccc       300
gggggttcat acgcccagg gggttcagga ggtccaggag gtgcagggg accatacgga       360
ccgggcggtg agggaccagg gggcgctggc ggaccctatg acctggcgg agctggaggt       420
ccctacgggc caggcgggc tggaggaccg tatggaccgg tggagaagg tggtccgtac       480
ggcccgggcg ggtcttacgg accaggtggc gcaggaggtc cttatgggcc gggtggacca       540
tacggtccag gcgagaggg tccaggtggg gcaggtgggc cttatggccc gggaggagtt       600
ggtccaggcg gcggtggtcc ggcgggtat ggcccgggtg gcgcaggtcc aggcggatat       660
ggaccaggtg gctctggacc cggagggtac gggccgggtg gttcagggcc tggaggttat       720
ggtccgggag gtagtggacc aggaggttat gggcctgggg gttcagggcc aggtggttat       780
ggtccaggag gatcaggtcc aggtggaagt ggtccagggg gttatggccc tggtggtagc       840
ggcccaggtg gcagtggacc gggaggatat ggcccaggag gttcaggtcc cggtggatac       900
ggaccgggtg gatctggacc aggcggttct ggtccgggag gttacggtcc tgggggtagt       960
ggtcccggag gtagtggacc aggtggatat ggaccaggag ggtctggacc cggaggtttt     1020
ggtccaggcg gatttggtcc tggtggttct gggcctggtg gtatggtcc tggcggatct     1080
ggtccaggtg gggcaggacc tggtggagtt ggacctgggg gttttggacc cggtggtgcg     1140
ggaccagggg gtgcaggtcc tggtggcgct ggtcctggag gcgctgggcc aggcggtgct     1200
ggacctggag gagcaggacc aggtggtgct ggccccggtg gcgcaggccc tggaggtgct     1260
ggtggagctg gtggtgcagg tggagcaggt ggttcaggag gagctggtgg ttcaggtgga     1320
actactataa tcgaagacct tgatattacg attgatggag cagatggtcc catcactatt     1380
tcggaagaat tgactatttc agcttattat ccatcatcta gagtgcctga tatggttaat     1440
ggaattatgt ctgcaatgca aggaagtggt tttaattatc aaatgtttgg taatatgttg     1500
tctcaatata gtagtggttc tggaacatgt aatccgaata atgtaaatgt tttaatggat     1560
gcgctgttag cggctttaca ttgtcttagt aatcatggat cctcatcatt tgctccgagt     1620
cctactccag cagctatgtc agcctatagc aattctgttg gtagaatgtt tgcttattaa     1680
```